(12) United States Patent
Callaway et al.

(10) Patent No.: US 8,682,431 B2
(45) Date of Patent: Mar. 25, 2014

(54) DRIVELINE CABLE ASSEMBLY

(71) Applicant: Thoratec Corporation, Pleasanton, CA (US)

(72) Inventors: Justin Aron Callaway, Goffstown, NH (US); Matthew Wagers, Cambridge, MA (US); James H. Baker, Westford, MA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/747,741

(22) Filed: Jan. 23, 2013

(65) Prior Publication Data

US 2013/0190551 A1   Jul. 25, 2013

Related U.S. Application Data

(60) Provisional application No. 61/589,929, filed on Jan. 24, 2012.

(51) Int. Cl.
*A61N 1/00* (2006.01)

(52) U.S. Cl.
USPC .......................................................... 607/16

(58) Field of Classification Search
USPC .......................................................... 607/16
See application file for complete search history.

(56) References Cited

U.S. PATENT DOCUMENTS

| | | | |
|---|---|---|---|
| 7,976,271 B2 * | 7/2011 | LaRose et al. | ................ 415/104 |
| 2005/0107658 A1 | 5/2005 | Brockway | |
| 2011/0160516 A1 | 6/2011 | Dague et al. | |

FOREIGN PATENT DOCUMENTS

| WO | WO0183021 A1 | 11/2001 |
|---|---|---|
| WO | WO2010025411 A2 | 3/2010 |

OTHER PUBLICATIONS

PCT Notification of Transmittal of the International Search Report and the Written Opinion for International Application No. PCT/US2013/022698 dated May 15, 2013, 15 pages.

* cited by examiner

*Primary Examiner* — Robert N Wieland
(74) *Attorney, Agent, or Firm* — Kilpatrick Townsend & Stockton LLP

(57) ABSTRACT

A blood pump assembly includes a blood pump configured for implantation and a cable assembly for providing power and control signals to the blood pump. The cable assembly includes a strain relief assembly and a driveline. The strain relief assembly secures the cable assembly to the blood pump and has an outer surface that is curved along a longitudinal extent of the strain relief assembly at least along an outer peripheral side of the outer surface. The strain relief assembly defines a compartment and an internal passage that leads to the compartment. The driveline houses a plurality of conductors that extend from the driveline through the internal passage and into the compartment.

19 Claims, 18 Drawing Sheets

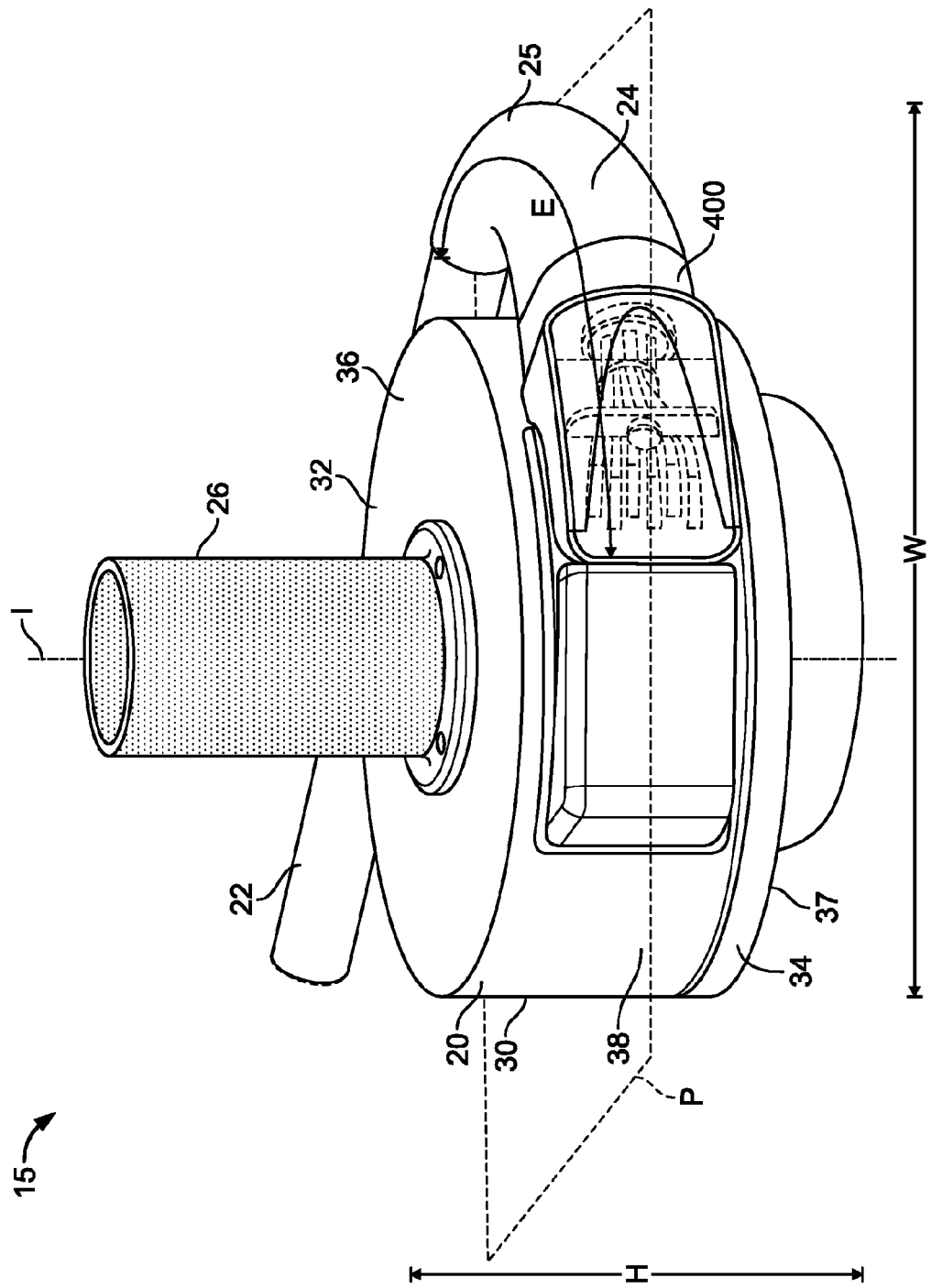

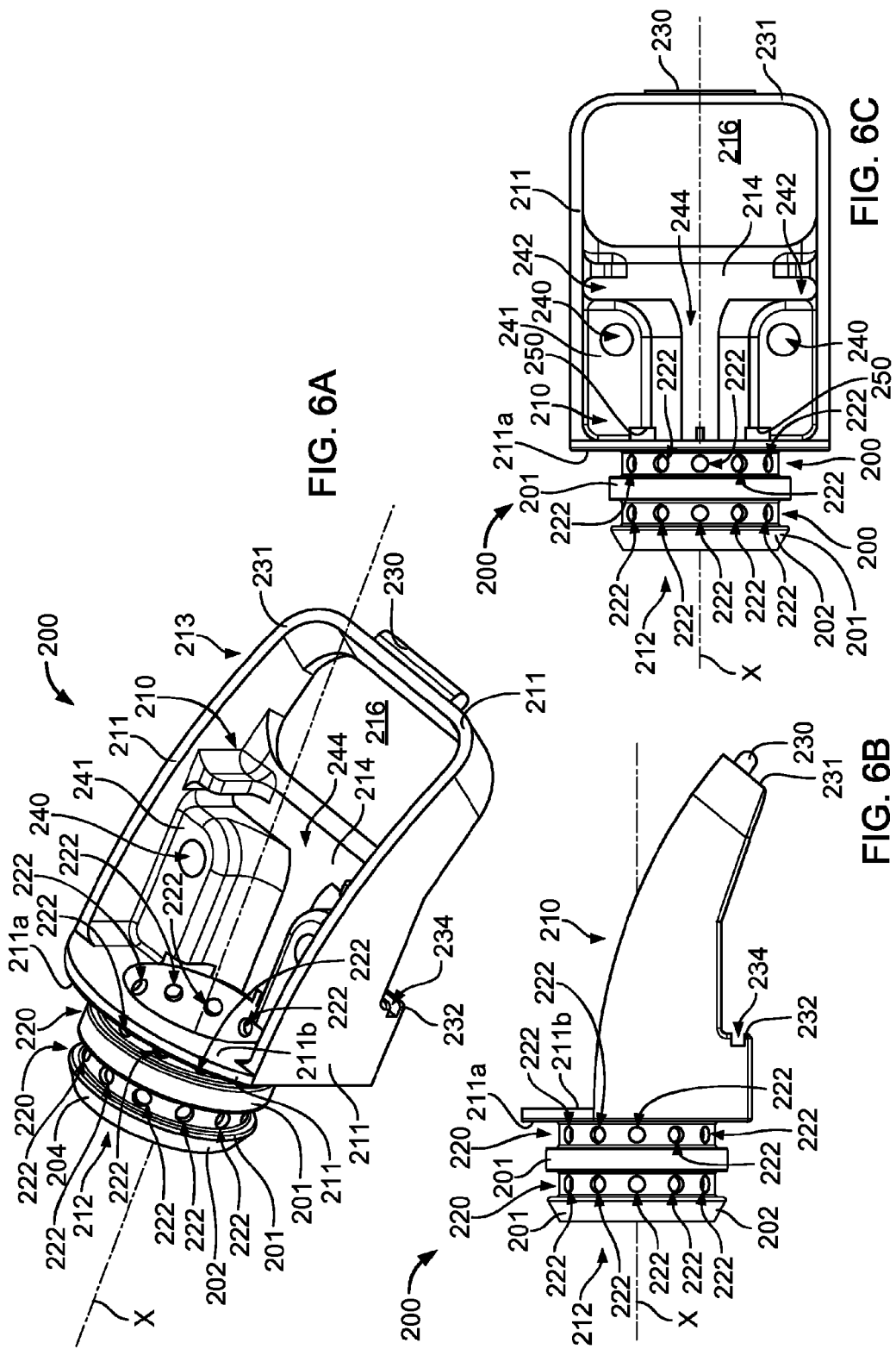

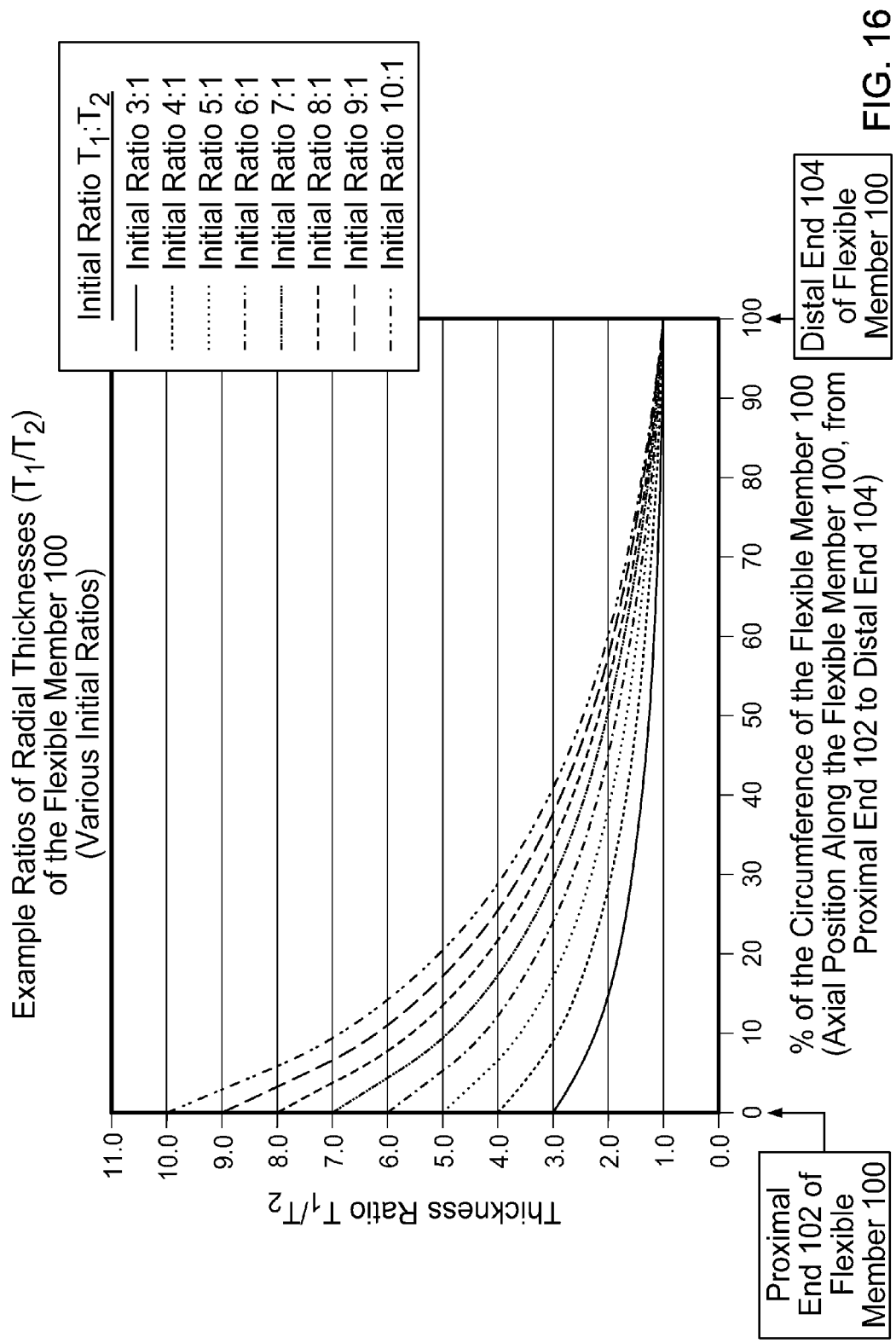

DRIVELINE CABLE ASSEMBLY

CROSS-REFERENCE TO RELATED APPLICATION

This application claims priority to and the full benefit of U.S. Provisional Patent Application No. 61/589,929, filed Jan. 24, 2012 and titled "DRIVELINE CABLE ASSEMBLY," which is incorporated herein by reference in its entirety.

FIELD

This description relates to driveline cable assemblies, for example, driveline cable assemblies for ventricular assist devices.

BACKGROUND

Ventricular assist devices, known as VADs, are blood pumps used for both short-term and long-term applications where a patient's heart is incapable of providing adequate circulation. A VAD can supplement a weak heart or can effectively replace the natural heart's function. For example, a patient suffering from heart failure may use a VAD while the patient awaits a heart transplant. In another example, a patient may use a VAD while the patient recovers from heart surgery. Some heart failure patients may have a VAD implanted for permanent use. VADs can be implanted in the patient's body and powered by an electrical power source outside the patient's body through a driveline cable assembly.

SUMMARY

In one general aspect, a blood pump system includes a strain relief assembly. The strain relief assembly includes a first member that defines a compartment and a second member that is more flexible than the first member. An outer side of the second member is curved and the second member defines an internal channel that leads to the compartment.

In a further aspect, according to any of the aspects above, the strain relief assembly is sized and positioned to lie entirely within a transverse footprint of the blood pump. The blood pump has an outlet portion that defines a fluid outlet axis and the strain relief assembly orients a driveline in a direction substantially parallel to the outlet axis.

In a further aspect, according to any of the aspects above, a cable including electrical conductors and an internal strength member extend through the internal channel into the compartment. The electrical conductors engage electrical connectors of the blood pump within the compartment, and the internal strength member is anchored to the strain relief assembly within the compartment.

In a further aspect, according to any of the aspects above, the internal passage has a substantially constant diameter along the longitudinal extent of the second member, and the second member has a wall thickness that decreases along the longitudinal extent.

In a further aspect, according to any of the aspects above, the first member has an annular portion that has an inner surface and an outer surface. The second member is molded about the outer surface of the annular portion. Holes are defined through the annular portion and the second member extends through the holes.

In a further aspect, according to any of the aspects above, the first member includes a surface oriented perpendicular to the internal passage configured to engage a cable to limit travel of the cable through the passage.

In a further aspect, according to any of the aspects above, a cross-section of the second member has a substantially D-shaped exterior at a proximal end region of the second member. A cross-section of the second member has a circular exterior at a distal end region of the second member. The second member has a wall thickness that gradually decreases between the proximal end region and the distal end region.

In one general aspect, a blood pump assembly includes a blood pump configured for implantation, and a cable assembly secured to the blood pump for providing power and control signals to the blood pump. The cable assembly includes a strain relief assembly and a driveline. The strain relief assembly secures the cable assembly to the blood pump and has an outer surface that is curved along a longitudinal extent of the strain relief assembly, at least along an outer peripheral side of the outer surface. The strain relief assembly defines a compartment and an internal passage that leads to the compartment. The driveline houses a plurality of conductors that extend from the driveline through the internal passage and into the compartment.

Implementations may include one or more of the following features. For example, the strain relief assembly is sized and positioned to lie entirely within a transverse footprint of the blood pump. The outer surface of the strain relief assembly has an inner peripheral side opposite the outer peripheral side, the inner peripheral side facing the blood pump and being spaced apart from the blood pump. The blood pump has an outer surface facing the inner peripheral side, and the inner peripheral side has a radius of curvature along the longitudinal extent that is larger than a radius of curvature of the outer surface of the blood pump along the longitudinal extent. The pump housing includes electrical connectors that extend into the compartment. The conductors are electrically connected to the electrical connectors of the pump housing, the conductors being oriented substantially transverse to the electrical connectors. The conductors are secured within the compartment by potting. The cable assembly includes an inner strength member that extends through the internal passage and is anchored to the strain relief assembly within the compartment. The blood pump has an outlet portion that defines an outlet axis and the cable assembly orients the driveline in a direction substantially parallel to the outlet axis, and the driveline is radially offset from the outlet portion by a distance of less than approximately 1 inch.

In one general aspect, an implantable strain relief assembly includes a first member that has an annular portion and an opening defined through the annular portion. The first member has a conductor mounting portion that defines a compartment in communication with the opening. The implantable strain relief assembly includes a second member that is more flexible than the first member. The second member has an end region coupled to the annular portion and has an outer surface that is curved along a longitudinal extent of the second member at least along a side of the outer surface. The second member defines an internal passage along the longitudinal extent leading to the opening defined through the annular portion of the first member. The internal passage has a substantially constant diameter along the longitudinal extent, and the second member has a wall thickness that decreases along the longitudinal extent.

Implementations may include one or more of the following features. For example, the annular portion has an inner surface and an outer surface, and the second member is molded about the outer surface. Holes are defined through the annular portion, and the second member extends through the holes.

The first member is configured to receive an anchor component in the compartment, and the anchor compartment is configured to secure an end of a cable to the first member. The first member includes a surface oriented perpendicular to the internal passage configured to engage a cable to limit travel of the cable through the passage.

In one general aspect, an implantable strain relief device includes a member having an outer surface that is curved along a longitudinal extent of the member at least along a side of the outer surface. The member defines an internal passage along the longitudinal extent having a substantially constant diameter along the longitudinal extent. The member has a wall thickness that decreases along the longitudinal extent, and at least a portion of the outer surface has a cross-sectional geometry that includes a rounded portion opposite a substantially flat portion.

Implementations may include one or more of the following features. For example, the outer surface is curved in an unloaded state of the member. The member has a distal end portion that has a cross-sectional geometry that is substantially circular. The outer surface of the member has a side that has a radius of curvature of between approximately 1 and approximately 3 inches along the longitudinal extent. A length of the member along the longitudinal extent is between approximately 2 and approximately 4 inches.

Various aspects of the invention are directed to a strain relief assembly comprising any of the features above in any combination.

In one general aspect, a method of providing strain relief at a blood pump includes forming a strain relief assembly having a curvature along a longitudinal extent of the strain relief assembly, positioning a driveline within the strain relief assembly, and connecting the strain relief assembly and the driveline to the blood pump at an outer wall of the blood pump that connects first and second opposing surfaces of the blood pump.

Implementations may include one or more of the following features. For example, connecting the strain relief assembly and the driveline includes orienting the strain relief assembly such that electrical connectors on the blood pump extend into a compartment defined by the strain relief assembly. The method includes establishing an electrical connection between conductors of the driveline and the electrical connectors in the compartment.

In one general aspect, a blood pump assembly includes a pump housing having an outer surface and defining a hermetically sealed compartment. The blood pump assembly includes a boss that extends from the outer surface of the pump housing and a feed-through component coupled to the boss. The feed-through component has electrical conductors that extend outward from the boss in a direction substantially perpendicular to the outer surface. The electrical conductors are configured to transmit electrical signals between the hermetically sealed compartment and a location outside the hermetically sealed compartment. The boss includes one or more attachment features configured to secure a driveline to the pump housing.

Implementations may include one or more of the following features. For example, a strain relief assembly engaged to the attachment features of the boss, the strain relief assembly defining a compartment and an opening that admits the electrical conductors into the compartment. A driveline extending through the strain relief assembly, the driveline having driveline conductors connected to the electrical conductors through ferrules. The connections of the ferrules with the driveline conductors and the electrical conductors are surrounded by potting, and the potting has at least one exposed side. The potting is exposed at a side facing away from the pump housing. The attachment features of the boss include one or more grooves defined in the boss, and the strain relief assembly includes one or more tabs located in the one or more tabs. The outer surface of the pump housing is substantially cylindrical, and the electrical conductors of the pump housing extend from the boss in a direction radially outward from the outer surface. The driveline includes an inner strength member coupled to the stress relief assembly through an anchor, the inner strength member being configured to transmit axial loads on the driveline to the stress relief assembly through the anchor.

Various aspects of the invention are directed to a method of manufacturing a strain relief assembly including forming a first member that defines a compartment; forming a second member that is more flexible than the first member and having an outer side that is curved, wherein the second member defines an internal channel that leads to the compartment. The method may include sizing and positioning the strain relief assembly to lie entirely within a transverse footprint of an associated implantable blood pump. The blood pump may have an outlet portion that defines a fluid outlet axis. The method may include orienting the strain relief assembly such that a driveline is in a direction substantially parallel to the outlet axis. Various aspects of the invention are directed to using an implantable pump including: positioning an implantable pump having a strain relief assembly according to any of the above in a body, and controlling the pump to pump blood from the heart to the circulatory system.

The details of one or more implementations are set forth in the accompanying drawings and the description below. Other features will be apparent from the description and drawings, and from the claims.

DESCRIPTION OF THE DRAWINGS

FIG. 2 is a perspective view of the blood pump assembly.

FIG. 6A is perspective view of a rigid member of the blood pump assembly.

FIG. 6B is a lateral view of the rigid member.

FIG. 6C is a top view of the rigid member.

FIG. 16 is an illustration of various examples of radial thickness ratios of the flexible member.

The details of one or more implementations are set forth in the accompanying drawings and the description below. Other features will be apparent from the description and drawings, and from the claims.

DETAILED DESCRIPTION

Figure 1A:
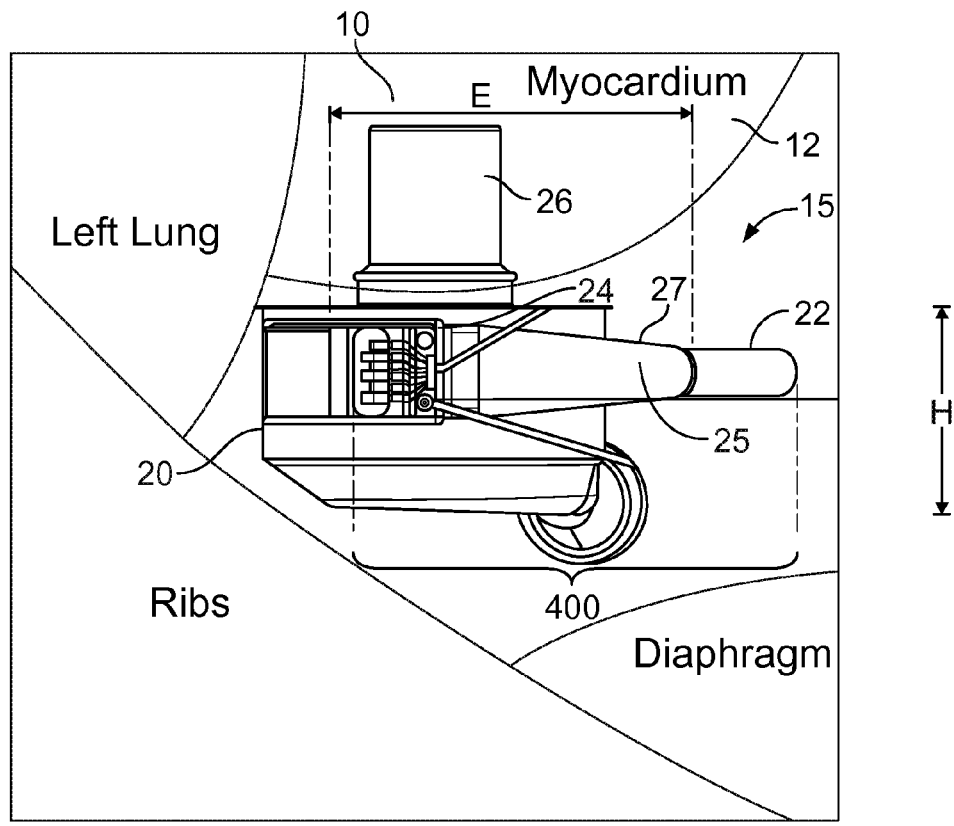
FIG. 1A is a side view of a blood pump assembly implanted at a heart.
Figure 1B:
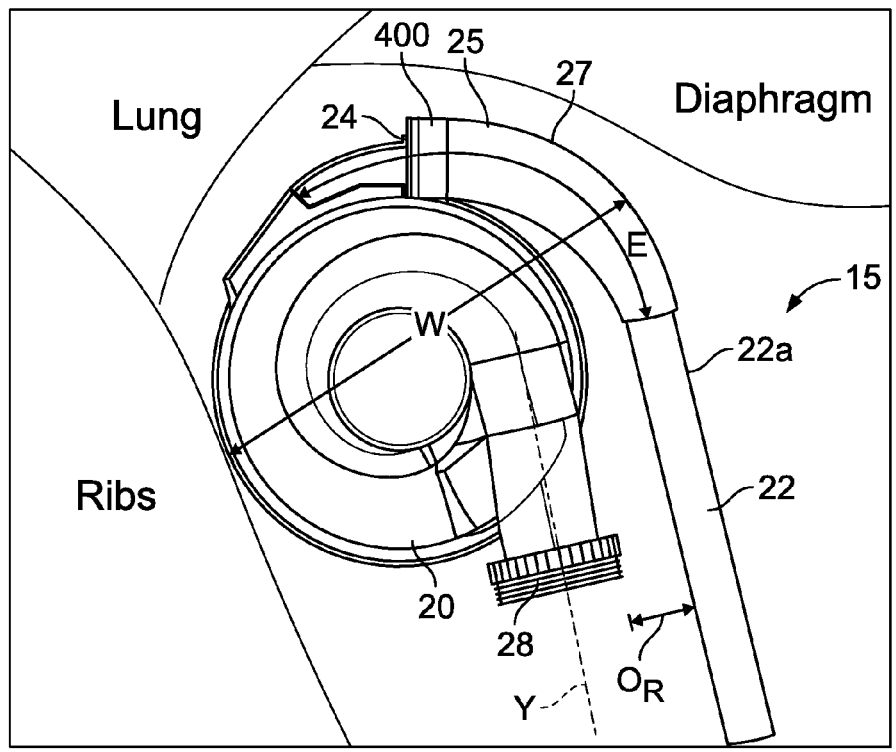
FIG. 1B is a bottom view of the blood pump assembly implanted at the heart.

Referring to FIGS. 1A and 1B, a blood pump assembly 15 can be implanted in a patient's body to supplement, or in some instances replace, the natural pumping function of a heart 10. The blood pump assembly 15 includes a blood pump 20 that is sized to be implanted in a patient's thoracic cavity, and a cable assembly 400 that is secured to the blood pump 20 for providing power and control signals to the blood pump 20. The cable assembly 400 includes a driveline 22 and a strain relief assembly 24. The driveline 22 houses conductors that carry the power and control signals. The strain relief assembly 24 secures the cable assembly 400 to the blood pump 20 and reinforces the driveline 22 to resist acute and chronic loading on the cable assembly 400.

The strain relief assembly 24 is curved in its unloaded state, that is, it is curved in its formed state without an applied bending force. For example, the strain relief assembly 24 is curved along its longitudinal extent, E, at least along an outer peripheral side 27 of an outer surface 25 of the strain relief assembly 24, for example, having a similar curvature as the pump housing circumferentially along the side facing away from the blood pump 20. In some implementations, the outer surface 25 is curved along at least the majority of the longitudinal extent, E, and the curvature extends away from the blood pump 20 to a distal end of the strain relief assembly 24.

During implantation of the blood pump assembly 15 and subsequent operation, the connection between the blood pump 20 and the driveline 22 is subject to a variety of stresses. The strain relief assembly 24 establishes a mechanical connection between the blood pump 20 and the driveline 22, strengthening and protecting the driveline 22 (and its electrical connections) against bending, twisting, and other loads (including flexural fatigue). As discussed further below, the mounting location and the curvature of the strain relief assembly 24 contribute to providing a low profile for the blood pump assembly 15, which facilitates placement in a body cavity constrained by, for example, the patient's ribs, diaphragm, and lungs. The low profile can be achieved by minimizing a height, H, of the blood pump assembly 15 and a width, W, of the blood pump assembly 15 while maintaining sufficient strength to withstand the long-term stresses of implantation.

In use, the blood pump 20 receives blood through an inflow cannula 26 of the blood pump assembly 15 that extends into, for example, a left ventricle 12 of the heart 10. The blood pump 20 supplies blood to the circulatory system of the patient, for example, to an aorta or a peripheral artery or peripheral vein. The outflow can be directed through an outflow cannula (not shown), attached at an outlet portion 28 of the blood pump 20. The blood pump assembly 15 can also be implanted such that the blood pump 20 receives blood from a right ventricle of the heart 10 and supplies blood to, for example, a pulmonary artery. The blood pump 20 can also be used for biventricular support with a second blood pump 20 or a blood pump of another type.

In some implementations, as shown in FIG. 1B, the strain relief assembly 24 orients the driveline 22 such that, without an applied load on the driveline 22, at least a portion of the driveline 22 extends substantially parallel to an outlet axis, Y, defined by the outlet portion 28 of the blood pump 20. For example, a portion 22a of the driveline 22 that extends outward from the strain relief assembly 24 extends along an axis parallel to the outlet axis, Y. In some implementations, the portion 22a may be substantially parallel to the outlet axis, Y, by extending along an axis that is within about 20 degrees or within about 10 degrees of the outlet axis, Y. The strain relief assembly 24 positions the portion 22a at a radial offset, $O_R$, from the outlet portion 28 of, for example, less than approximately 1 inch, or between approximately 0.25 and approximately 0.50 inches. In this orientation, the strain relief assembly 24 has a curvature about the blood pump 20 that is similar to the curvature of the outer circumference of the blood pump 20, and the driveline 22 is oriented parallel to the outlet portion 28 and extends from the blood pump 20 in the same direction as the outlet portion 28. This orientation promotes anatomical efficiency in placement of the blood pump 20 by reducing the space that needs to be created in the thoracic cavity to accommodate different extensions from the blood pump 20.

Different relative positions of the outlet portion 28 and the driveline 22 can facilitate other implantation techniques. For example, for a left thoracotomy or for some minimally invasive approaches, the outflow of the pump 20 is oriented toward the descending aorta during implantation. To accommodate this placement of the blood pump 20, the strain relief assembly 24 orients the driveline 22 in a direction opposite the outlet portion, for example, extending from an opposite side of the blood pump 20 rather than from the same side. In this configuration, the driveline 22 extends along an axis substantially parallel to the outlet axis defined by the outlet portion 28, but in an opposite direction on an opposite side of the blood pump 20.

Referring to FIG. 2, the blood pump 20 includes a pump housing 30 that contains a motor (not shown). The pump housing 30 includes an upper portion 32 and a bottom cover 34 welded together to form a hermetically sealed compartment about the motor. The upper portion 32 of the pump housing 30 has a top surface 36 opposing a bottom surface 37 of the bottom cover 34. The upper portion 32 also includes an outer wall 38 to which the strain relief assembly 24 is mounted. The outer wall 38 can be a curved circumferential surface, for example, a generally cylindrical shape. The inflow cannula 26 extends from the top surface 36 of the pump housing 30, in a direction generally perpendicular to the top surface 36.

To attach the blood pump 20 to the heart 10, an anchoring component such as a sewing ring (not shown) can be attached to cardiac tissue. The inflow cannula 26 is inserted through an opening in the sewing ring and through an opening in the cardiac tissue. The sewing ring is then fastened about the inflow cannula 26 with a clamp or other fastener. Various methods and apparatuses for such anchoring are disclosed in U.S. patent application Ser. No. 12/650,017, filed Dec. 30, 2009, and U.S. Patent Application Ser. No. 61/448,434, filed on Mar. 2, 2011, each of which are hereby incorporated herein by reference for all purposes.

The driveline 22 attaches to the blood pump 20 on the outer wall 38 of the pump housing 30. The strain relief assembly 24 curves circumferentially about a portion of the outer wall 38, along the circumference of the pump housing 30, minimizing the increase in the overall width, W, of the blood pump assembly 15 from the addition of the driveline 22. The strain relief assembly 24 and the pump housing 30 lie within a plane, P, generally perpendicular to an inflow axis, I, defined by the inflow cannula 26 with the strain relief assembly 24 positioned to be within a transverse footprint of the pump housing 30 to limit any increase in the overall height, H, of the pump housing 30. To limit potential abrasion caused by contact between the strain relief assembly 24 and the outer wall 38 of the pump housing 30, the strain relief assembly 24 can be spaced from the outer wall 38.

Figure 3:
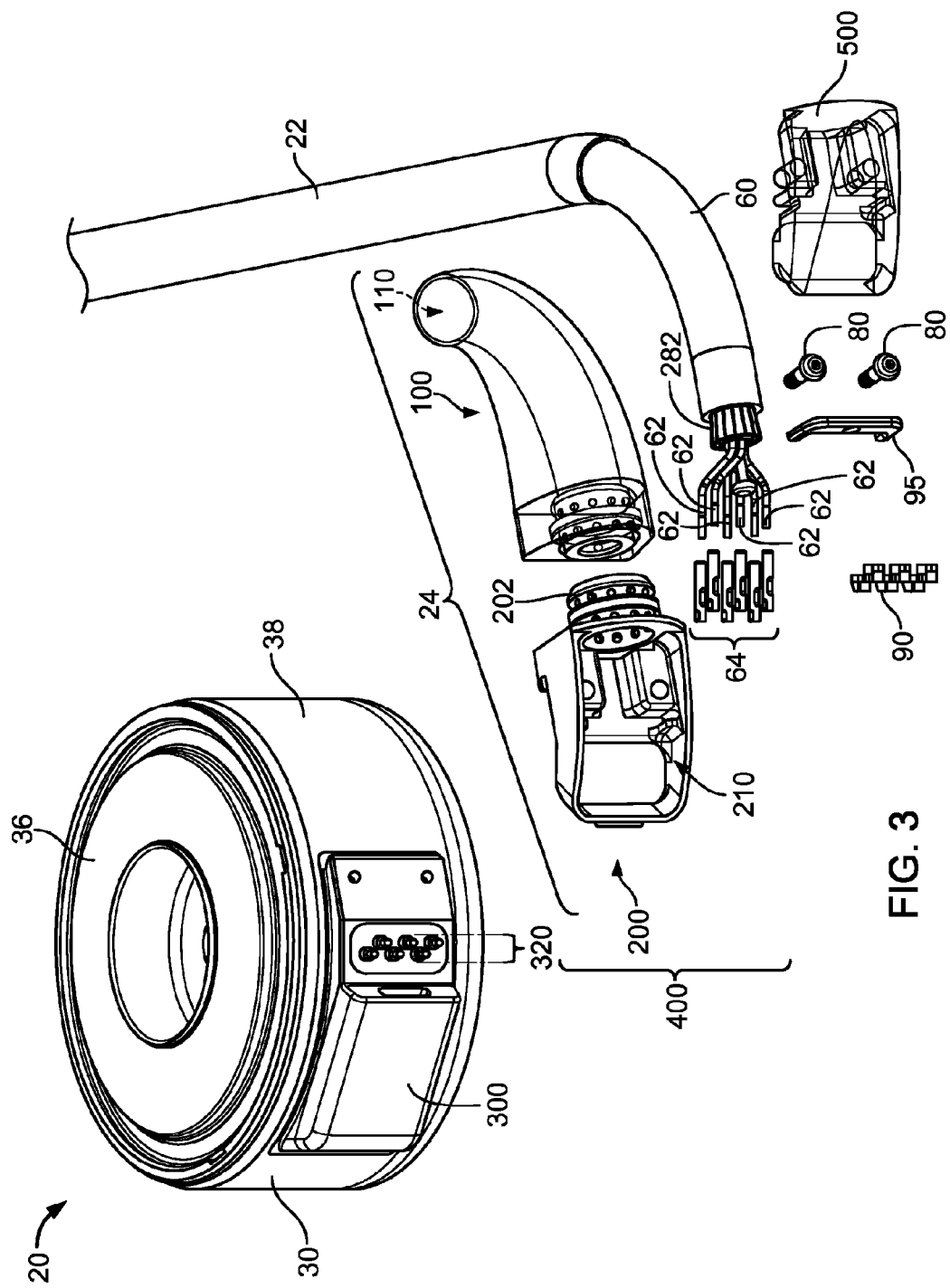
FIG. 3 is an exploded perspective view of the blood pump assembly.

Referring to FIG. 3, exemplary strain relief assembly 24 includes a first, rigid member 200 and a second, flexible member 100 that is more flexible than the rigid member 200. As described further below, the strain relief assembly 24 is formed by coupling the flexible member 100 to the rigid member 200, for example, by molding the flexible member 100 onto a portion 202 of the rigid member 200. An end portion 60 of the driveline 22 is secured within the strain relief assembly 24, and the cable assembly 400 is connected to the pump housing 30 to form mechanical and electrical connections to the pump housing 30. The flexible member 100 limits stresses on the driveline 22 and distributes forces away from the connection of the driveline 22 with the blood pump 20.

To form the mechanical and electrical connections, the rigid member 200 attaches to a boss 300 (e.g., a protruding feature) of the pump housing 30, with electrical contact pins 320 of the boss 300 extending into a compartment 210 defined in the rigid member 200. Conductors 62 housed within the driveline 22 also extend into the compartment 210 and are electrically connected to the pins 320. Other components, including ferrules 64, a ferrule carrier 90, and an anchor 95, each described further below, are also received in the compartment 210.

After the electrical and mechanical connections are established, potting, such as an epoxy, is introduced into the compartment 210 to secure the connections. The potting cures to form a potting plug 500 that secures the terminations of the driveline 22. When movement of the driveline 22 occurs, the potting plug 500 transmits loads on the conductors 62 to the strain relief assembly 24 rather than permitting the load to be transmitted through the conductors 62, ferrules 64, and pins 320. The potting that forms the potting plug 500 also becomes entangled with fibrous components of the driveline 22, such as a mesh or braided armor layer 282, which further strengthens the mechanical connection between the driveline 22 and the blood pump 20. In various embodiments, the potting plug is formed as a distinct unit from the driveline and pump housing. In various embodiments, the potting plug 500 limits moisture ingress that might otherwise result in undesired electrical connections between the pins 320 or between the pins 320 and metal components of the pump assembly, such as the pump housing 30. In various embodiments, the potting plug is configured to electrically isolate the internal components.

Figure 4A:
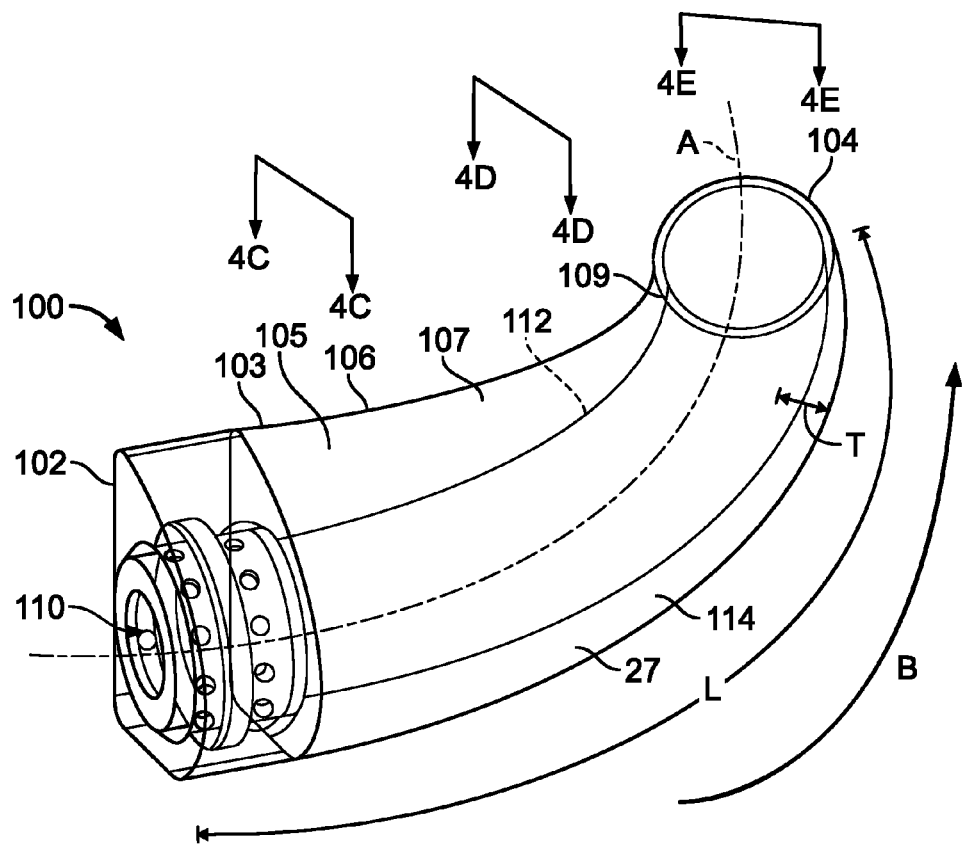
FIG. 4A is a perspective view of a flexible member of the blood pump assembly.

Referring to FIG. 4A, the flexible member 100 of the strain relief assembly 24 is dimensioned to protect the end region 60 of the driveline 22. The flexible member 100 fits over the driveline 22 and limits bending and twisting of the driveline 22. The flexible member 100 is formed to withstand stresses of long-term implantation that occur during, for example, an implantation period of five years, ten years, or longer. Over such periods, postural changes of a patient can result in more than one million loading cycles, more than two million loading cycles, or more. The flexible member 100 is also formed to withstand other in-vivo stresses that occur due to, for example, cardiac contractions and respiration of the patient. The flexible member 100 is also designed to withstand other stresses, such as weight gain or weight loss of the patient and traumatic driveline events such as accidents. The flexible member can also be configured to provide damping, electrical resistance, and/or shock resistance for the internal components. The flexible member thus can be selected and configured to achieve desired properties for a number of purposes as will be further described below.

The flexible member 100 is formed of a resilient material, for example, silicone, a silicone copolymer, or another polymer material. Liquid silicone rubber (LSR) silicone or high consistency rubber (HCR) silicone can be used. Flexible member 100 may be formed of other materials as would be understood by one of skill in the art from the description herein including, but not limited to, copolymers (e.g. polyurethane silicone, polycarbonate urethane silicone, and polyetherurethane silicone), elastomers, and thermoplastic elastomers (TPE). Suitable TPEs include, but are not limited to, polyether block amides such as PEBA and PEBAX. The material properties can also be modified by the use of various manufacturing techniques and treatments such as doping, the addition of various treatment agents, thermal treatments, and the like. The resilient material of the flexible member 100 can have one or more of the following material properties: durometer of approximately 20 to approximately 70 Shore A, or durometer of approximately 40 to approximately 60 shore A; tear strength of greater than approximately 40 kilonewtons per meter (kN/m), or tear strength of greater than approximately 50 kN/m; tensile strength of greater than 8 megapascals (MPa), or tensile strength of greater than approximately 10 MPa; and elongation at break of greater than 500%.

The flexible member 100 has a longitudinal extent or length, L, between a proximal end 102 and a distal end 104. In some implementations, the length, L, is between approximately 0.25 inches and approximately 4 inches. When the flexible member 100 is coupled to the rigid member 200, the length, L, extends along the longitudinal extent, E, of the strain relief assembly 24 (not shown). The flexible member 100 also has an outer surface 105, which forms the outer surface 25 of the strain relief assembly 24. When the flexible member 100 is coupled to the blood pump 20, a surface 106 of the flexible member 100 faces toward the outer wall 38 of the pump housing 30, and the surface 27 of the flexible member 100 faces away from the outer wall 38. In some implementations, the flexible member 100 is sized such that it extends between approximately 45 degrees to approximately 180 degrees about the circumference of the outer wall 38 of the pump housing 30 when the strain relief assembly 24 is coupled to the pump housing 30.

Figure 4B:
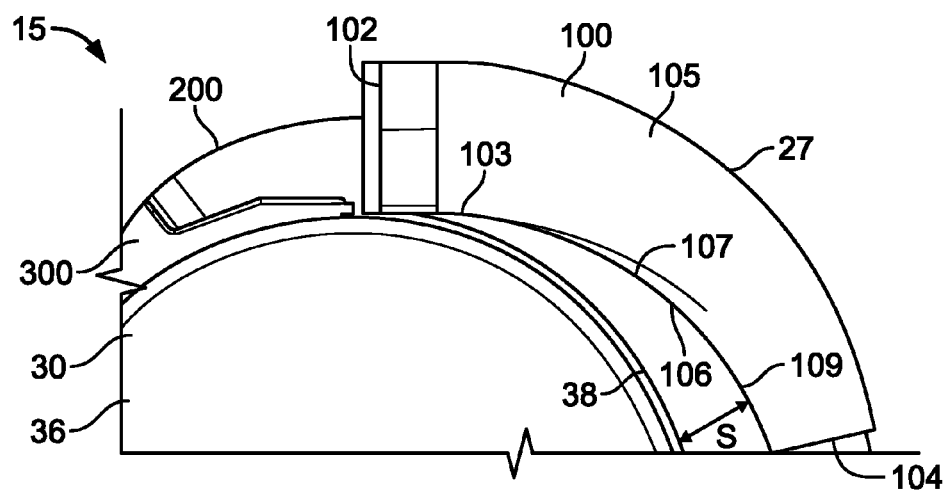
FIG. 4B is a top view of the blood pump assembly.

Referring to FIG. 4B, exemplary flexible member 100 is curved along the length, L, at least along the surface 27. The surface 106 can also be curved along the length, L. The flexible member 100 can extend about the outer wall 38 of the pump housing 30, generally tracking the curvature of the outer wall 38. In some implementations, the surface 27 of the flexible member 100 has a radius of curvature along the length, L, of approximately 0.5 to approximately 4 inches, or between approximately 1 and approximately 3 inches, or approximately 2 inches. The surface 106, as well as the general shape of the flexible member 100, can be formed to have a radius of curvature selected from the ranges and values described for the surface 27. In some implementations, the surface 106 is curved along at least a majority of the length, L, or along the entire length, L. The curvature may extend to the proximal end 102 and/or the distal end 104.

The radius of curvature of the flexible member 100 is greater than a radius of curvature of the outer wall 38 of the pump housing 30. When attached to the blood pump 20, the spacing, S, between the surface 106 of the flexible member 100 and the pump housing 30 increases from the proximal end 102 to the distal end 104. At the proximal end 102, the space, S, can be approximately 0.1 inches or less. At the distal end 104, the space, S, can be between approximately 0.2 inches and approximately 1 inch, or more particularly, between approximately 0.4 inches and approximately 0.6 inches.

Referring again to FIG. 4A, exemplary flexible member 100 defines an internal passage 110 between the proximal end 102 and the distal end 104, for example, through a central longitudinal axis, A, of the flexible member 100. The internal passage 110 is defined by a wall 114 having a tubular inner surface 112 that has a cross-sectional diameter of between, for example, approximately 0.05 inches to approximately 0.6 inches. The diameter of the internal passage 110 can be substantially constant along the length, L, of the flexible member 100 (e.g., varying less than 30%, or less than 15% along the length, L). The thickness, T, of the wall 114 measured radially outward from the tubular inner surface 112 decreases or tapers along the length, L, in a direction, B, from the proximal end 102 to the distal end 104.

Because the wall 114 is thickest near the proximal end 102, resistance to flexion at the proximal end 102 (near the connection of the driveline 22 with the pump housing 30) is greater than at the distal end 104. The thickness, T, can decrease substantially continuously along the length, L, of the flexible member 100. Consequently, the flexibility of member 100 can vary along its length, L, having increasing flexibility where the wall thickness decreases and having decreasing flexibility where the wall thickness increases. For example, the thickness, T, can decrease with a taper angle of for example, between approximately 1 degree to approximately 5 degrees, or between approximately 2 degrees and approximately 4 degrees, or at approximately 3 degrees. Because the diameter of the internal passage 110 is substantially constant along the length, L, the outer dimensions of the flexible member 100 decrease along the length, L, as the thickness of the wall 114 decreases.

The flexible member 100 can be non-axisymmetric, or in other words, lacks rotational symmetry about the central longitudinal axis, A. For example, at a proximal portion 103, the thickness of wall 114 varies about the axis, A. As illustrated, at the proximal portion 103, the surface 27, which faces away from the pump housing 30, is rounded circumferentially about the axis, A, and the surface 106, which faces the pump housing 30, is substantially flat. As described further below, the non-axisymmetric shape can contribute to increased durability and strain relief performance compared to an axisymmetric shape. For example, stress and strain are decreased, and propensity for twisting when a lateral load is applied (e.g., in a direction parallel to the inlet axis, I, of FIG. 2) is decreased for the non-axisymmetric shape compared to the axisymmetric shape. However, in an alternate embodiment, an axisymmetric shape may be more desirable if permitting a limited degree of rotation is perceived to be a benefit.

Figure 4C:
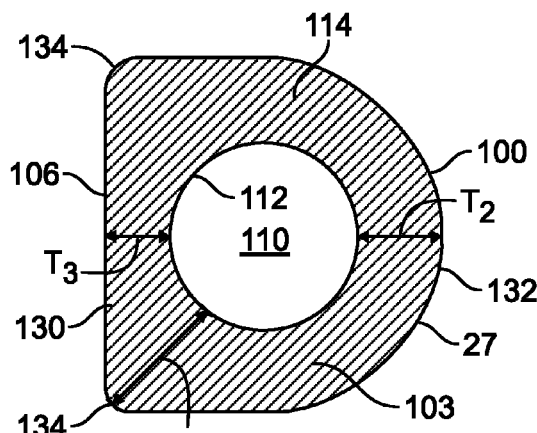
FIG. 4C is a cross-sectional view of the flexible member taken at line 4C-4C of FIG. 4A.
Figure 4D:
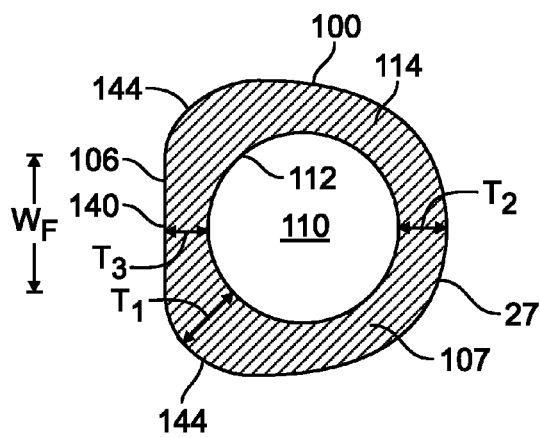
FIG. 4D is a cross-sectional view of the flexible member taken at line 4D-4D of FIG. 4A.

Referring to FIG. 4C, a cross-section of exemplary flexible member 100 at the proximal portion 103, taken perpendicular to the axis, A, illustrates the asymmetry of the flexible member 100. The cross-section has a substantially flat edge 130 at the surface 106 and a rounded edge 132 at the surface 27, resulting in a D-shaped exterior. In some implementations, at least a majority of the edge 130 is, or 80% or more of the edge 130, is straight (e.g., linear). At corner portions 134 located adjacent to the flat edge 130, a radial thickness, $T_1$, of the wall 114 is greater than a radial thickness, $T_2$, of the wall 114 at the rounded edge 132. In some implementations, the thickness is increasing from $T_1$ to $T_2$. In some implementations the thicknesses are non-uniform. In some implementations, along a portion of the flexible member 100 or along the entire flexible member 100, the thickness, $T_1$, is the largest radial thickness at a given cross-section, and the thickness, $T_2$, is the smallest radial thickness at that cross-section. The greater thickness, $T_1$, at the corner portions 134 permits the flexible member 100 to resist twisting and other loads more than, for example, a wall 114 with a constant thickness equal to the thickness, $T_2$. Because of the location of the flat edge 130 relative to the pump housing outer wall 38 (facing inward toward the outer wall 38), any adverse impact of the additional thickness on the pump profile is minimized. In some implementations, the ratio $T_1:T_2$ at the proximal end 102 is between approximately 3:1 and approximately 10:1. In some implementations, the ratio $T_1:T_2$ at the proximal end 102 is between approximately 4:1 and approximately 5:1.

Referring to FIGS. 4B-4E, between the proximal end 102 and the distal end 104, the outer dimensions of the flexible member 100 transition from having a D-shaped cross-sectional geometry (FIG. 4C) at the proximal portion 103 to having a substantially circular cross-sectional geometry (FIG. 4E) at a distal portion 109. A transition portion 107 of the flexible member 100 between the proximal portion 103 and the distal portion 109 (FIG. 4D) illustrates how the width, $W_F$, of a flat edge 140 on the surface 106 decreases, and corner regions 144 become increasingly rounded.

Figure 4E:
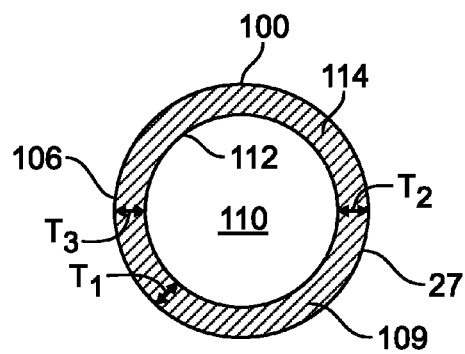
FIG. 4E is a cross-sectional view of the flexible member taken at line 4E-4E of FIG. 4A.

Due to this transition along the length, L, of the flexible member 100, the ratio $T_1:T_2$ diminishes along the axis, A, in a direction from the proximal end 102 to the distal end 104. This ratio can be, for example, the ratio between a maximum radial thickness at a given axial position and the minimum radial thickness at that axial position. From a maximum ratio of $T_1:T_2$ at the proximal portion 103, the ratio is gradually reduced to approximately 1:1 at the distal portion 109 (for example, at or near the distal end 104). As shown in FIG. 4E, the ratio of the thickness $T_1:T_2$ at the distal portion 109 is approximately 1:1, which helps uniformly distribute stress on the driveline 22 and impedes twisting of the driveline 22 when the driveline 22 is placed within the flexible component 100. The ratio $T_1:T_2$ can be reduced such that the ratio decreases more rapidly over the proximal portion 103 than over the distal region 109. For example, the ratio $T_1:T_2$ can decrease logarithmically along the length, L, of the flexible member 100, as shown in FIG. 16. As a result, the ratio $T_1:T_2$ is closer to 1:1 than the maximum ratio along the majority of the length, L, of the flexible member 100.

In some implementations, a radial thickness, $T_3$, that extends perpendicular to the substantially flat edge 130 is substantially the same as (e.g., within 20% of, or within 10% of) the thickness, $T_2$, at the same axial position along the axis, A. This relationship may occur along a portion of or along the entire length, L, of the flexible member 100. Because the thickness, $T_3$, is oriented radially outward from the outer wall 38 of the pump housing 30, maintaining the thickness similar to the thickness, $T_2$, helps reduce the overall profile of the pump 20.

In some implementations, a maximum thickness of the wall 114 is between approximately 0.02 and approximately 0.08 inches, or between approximately 0.04 and approximately 0.06 inches. As stated above, the thickness of the wall 114 and the shape of the flexible member 100 can be selected to withstand more than one million loading cycles, more than two million loading cycles, or more, where each loading cycle includes application of at least one foot-pound of load to the flexible member 100 while the proximal end 102 is secured. Each loading cycle can include axial deflection, circumferential deflection, or both. Axial deflection can include, for example, force applied to the flexible member 100 along the inlet axis, I, of the blood pump 20 (see FIG. 2). Circumferential deflection can include, for example, force applied to the flexible member 100 in a direction radially outward from the outer wall 38 of the pump housing 30.

Figure 5B:
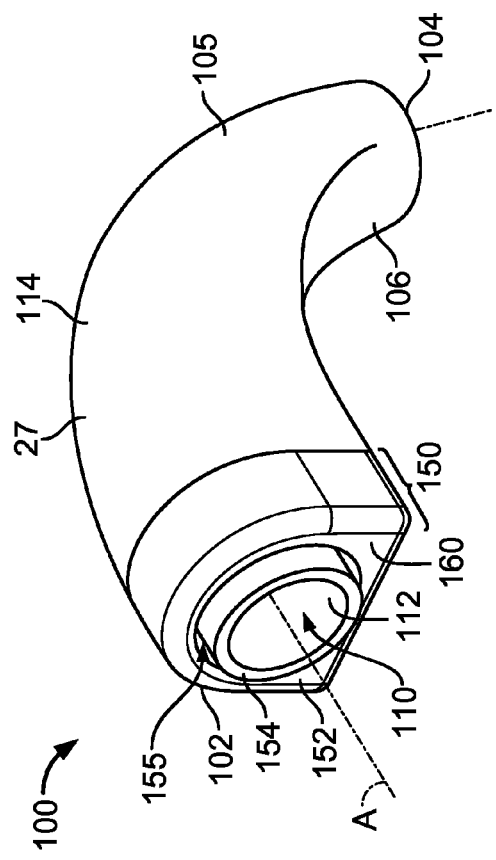
FIG. 5B is a perspective view of the flexible member.
Figure 5A:
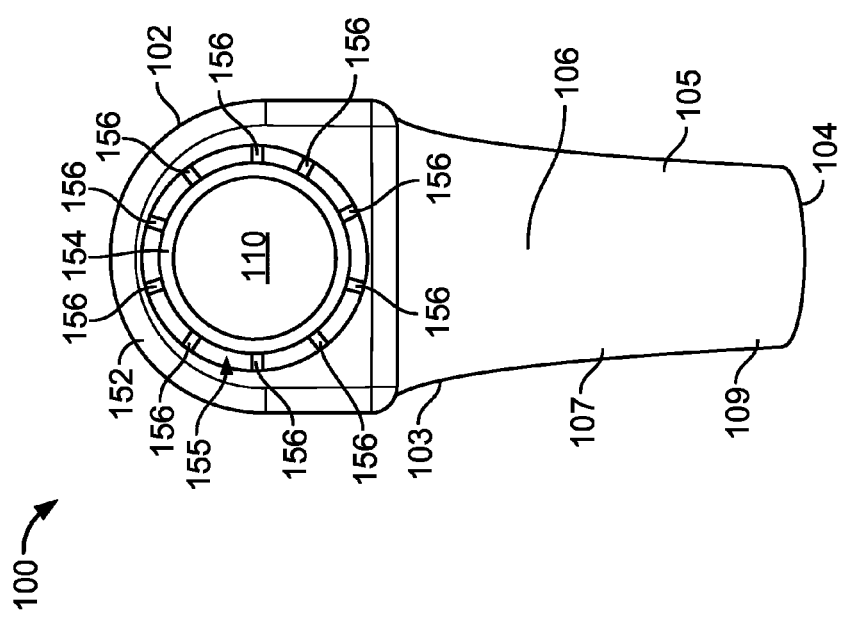
FIG. 5A is a proximal end view of the flexible member.

Referring to FIGS. 5A and 5B, during the molding process, an attachment portion 150 is formed at the proximal end 102 of the flexible member 100 that captures the rigid member 200. The attachment portion 150 is formed with an outer wall 152 and an inner wall 154 defining an annular space 155 in which the annular portion 202 of the rigid member 200 is located. Between the outer wall 152 and the inner wall 154, connecting links 156 extend through the annular portion 202 to lock the flexible member 100 in place relative to the rigid member 200, as described further below.

The materials mentioned above that form the flexible member (e.g., silicone and silicone copolymers) are well suited to provide strain relief, but may not adhere well to more rigid materials. The exemplary connecting links 156 provide mechanical attachment of the flexible member 100 to the rigid member 200 in a manner that relies on the tensile strength, elongation at break, and tear strength of the material of the flexible member 100 (e.g., silicone or silicone copolymers), thus decreasing the risk of dislodgement of the flexible member 100 from the rigid member 200.

Referring to FIG. 6A, the annular portion 202 of the rigid member 200 provides attachment features over which the flexible member 100 is molded. One or more circumferential grooves 220 are defined around the exterior of the annular portion 202, for example, between circumferential ridges 201 about the annular portion 202. Holes 222 are defined radially through the annular portion 202. When the flexible member 100 is molded onto the rigid member 200, material flows into the grooves 220, thereby forming rings that secure the annular portion 202 to the flexible member 100, and into the holes 222, thereby forming the connecting links 156. The material in the grooves 220 and the holes 222 impede removal of the flexible member 100 from the rigid member 200 in the event of, for example, axial loading. In some implementations, a primer is applied to the annular portion 202 before the flexible member 100 is formed, which can promote adhesion of the flexible member 100 to the annular portion 202.

The rigid member 200 can be an integral component formed of, for example, an implantable metal such as titanium. The rigid member 200 can be formed of the same material as the boss 300 and the pump housing 30, thus reducing possibility for corrosion or unequal thermal expansion at the interface of the rigid member 200 with the boss 300.

The rigid member 200 defines the compartment 210 between lateral walls 211. The annular portion 202 defines an opening 212 along a central axis, X, leading into the compartment 210. The compartment 210 is open at a top side 213, and an opening 216 is defined at the bottom of the compartment 210 through a bottom wall 214 of the rigid member 200. The opening 216 is located such that when the rigid member 200 is attached to the boss 300, the opening 216 is disposed over the electrically conductive pins 320. The lateral walls 211 and the bottom wall 214 form a conductor mounting portion in which electrical connections with the conductors 62 are established.

The lateral wall 211 from which the annular portion 202 extends includes an outer surface 211a that is oriented perpendicular to the axis, X, and extends completely about the annular portion 202. During molding of the flexible member 100 onto the annular portion 202, the outer surface 211a and an opposite inner surface 211b act as shut-offs against which the proximal end 102 of the flexible member 100 is formed. In some implementations, an optional layer 180 of the flexible member 100 can be molded on the inner surface 211b (see FIG. 12).

Referring also to FIG. 6B, the rigid member 200 includes extensions or tabs 230, 232 that engage the boss 300 to connect the rigid member 200 to the boss 300. The tab 230 extends from a proximal end 231 of the rigid member 200, which is located opposite the annular portion 202. For example, the tab 232 is located on the bottom of the rigid member 200, underneath the compartment 210. The tab 232 is shaped as a rail and extends toward the proximal end 231 in a direction parallel to the axis, X. Above the tab 232, the rigid member 200 defines a groove 234 for attachment to the boss 300.

Referring to FIG. 6C, within the compartment 210, the rigid member 200 defines holes 240 that admit the screws 80 or shear pins that limit disengagement of the rigid member 200 from the boss 300, as described further below. The holes 240 are defined through raised portions 241 that extend from the bottom wall 214. Near the opening 212, the raised portions 241 have surfaces 250 oriented perpendicular to the axis, X. The surfaces 250 are configured to engage an end of the driveline 22 to limit travel of the driveline 22 into the compartment 210.

Also within the compartment 210, the rigid member 200 defines slots 242 oriented perpendicular to the axis, X, that receive the anchor 95. The internal walls that define the slots 242 extend partially inward from the lateral walls 211, leaving an unobstructed central channel 244 in the compartment 210 to accommodate the conductors 62 of the driveline 22.

Figure 7A:
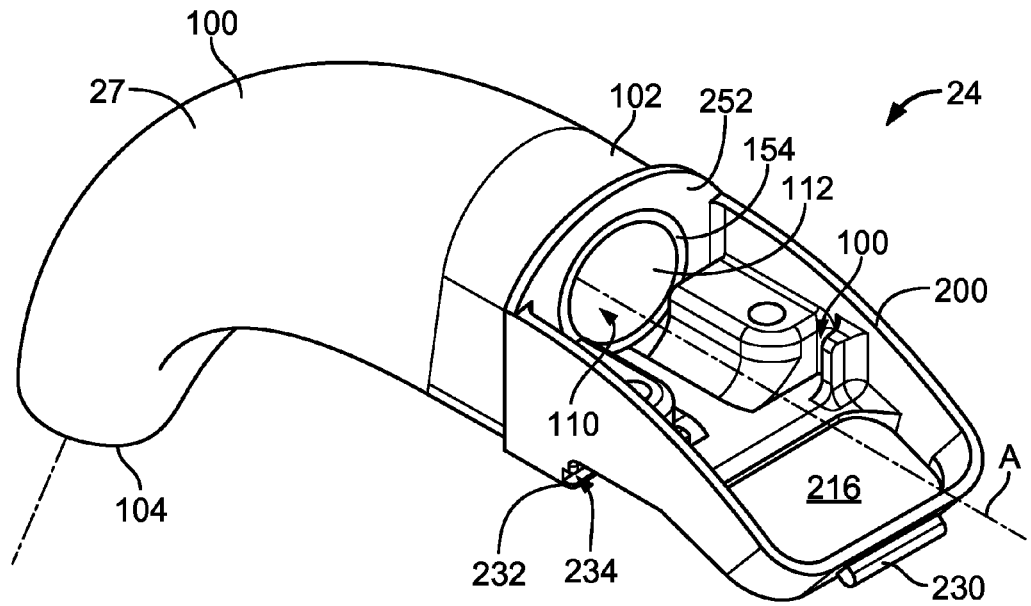
FIG. 7A is a perspective view of a strain relief assembly of the blood pump assembly.

Referring to FIG. 7A, the strain relief assembly 24 includes the flexible member 100 molded onto the rigid member 200. The flexible member 100 defines the internal passage 110 through the opening 212 in the annular portion 202, such that the internal passage 110 leads to the compartment 210.

Figure 7B:
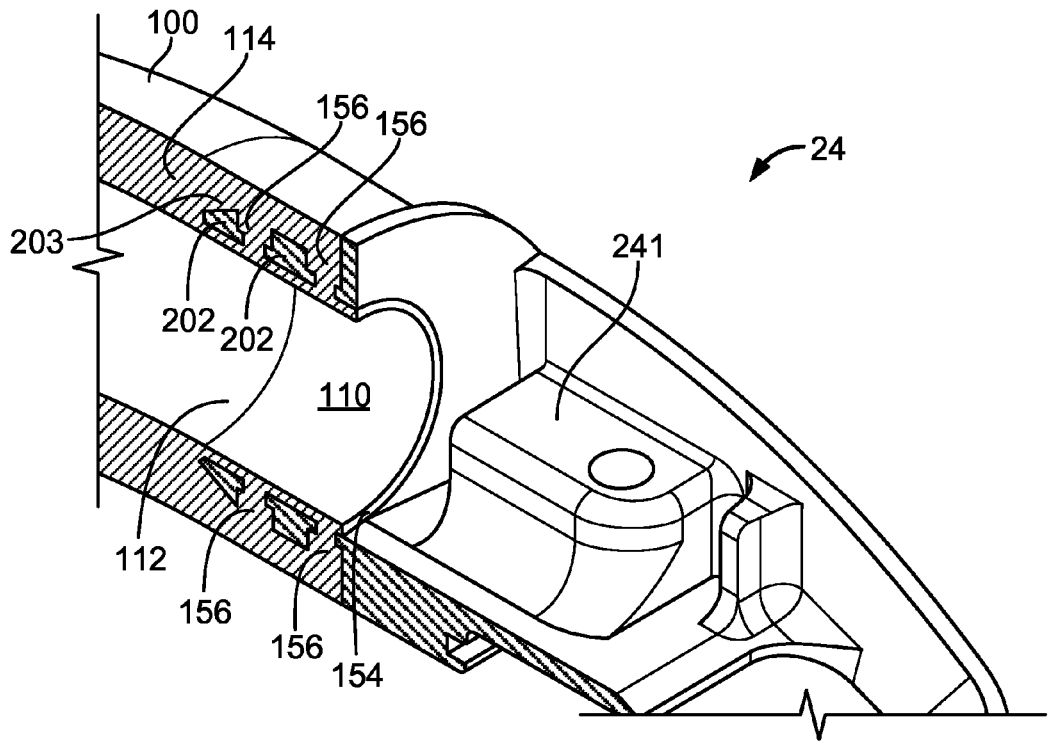
FIG. 7B is a cutaway view of the strain relief assembly.

Referring to FIG. 7B, the strain relief assembly 24 receives the driveline 22 to form the cable assembly 400 that attaches to the pump housing 30. After a silicone adhesive or other bonding agent is applied to the tubular inner surface 112 of the flexible member 100, the driveline 22 is advanced through the internal passage 110. The presence of the inner wall 154 of the flexible member 100 within the annular portion 202 facilitates bonding to the driveline 22 and cushions internal edges of the rigid member 200 that might otherwise impinge on the driveline 22. The annular portion 202 has an end 203 that is tapered, which reduces stress concentrations in the flexible member 100 around the end 203.

Figure 8A:
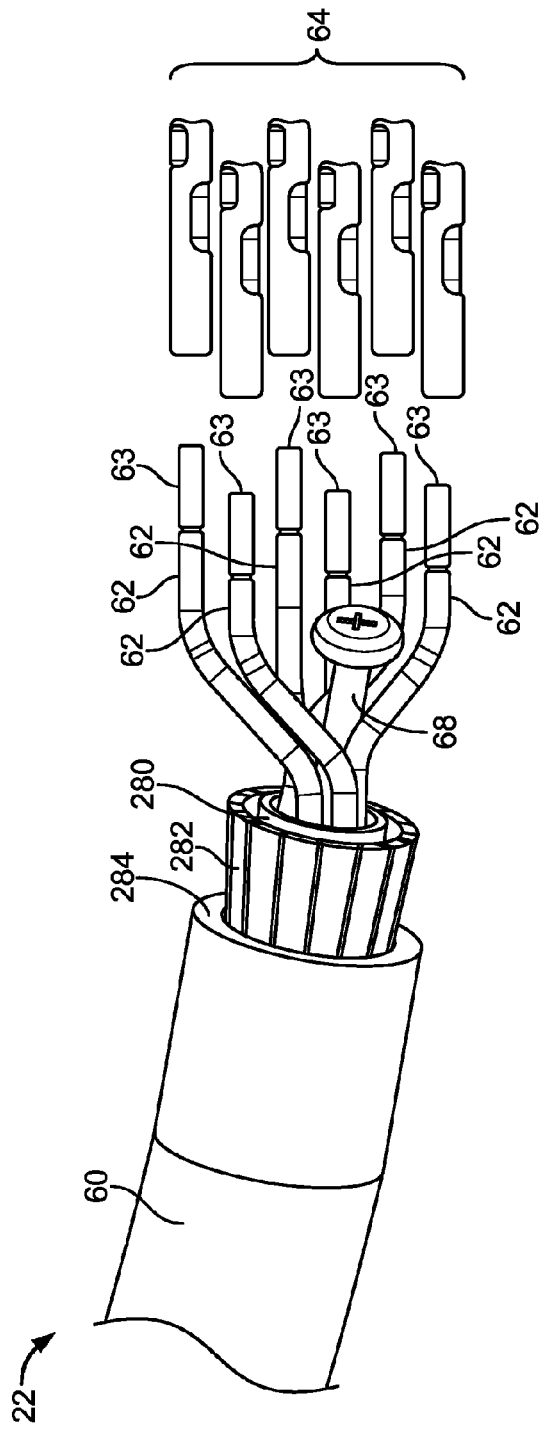
FIG. 8A is an exploded perspective view of a proximal end of a driveline of the blood pump assembly and ferrules.

Referring to FIG. 8A, the driveline 22 includes, for example, an inner strength member 68, the conductors 62, a covering (not shown), an inner jacket 280, the armor layer 282, and an outer jacket 284. The driveline 22 can include features as described in U.S. patent application Ser. No. 13/314,806, filed on Dec. 8, 2011, which is hereby incorporated by reference in its entirety. The inner strength member 68 is formed, for example, of braided ultra-high molecular weight polyethylene, or other lightweight, flexible material with high tensile strength and provides resistance to axial breakage of the driveline 22. The conductors 62 are disposed about the inner strength member 68, for example, wrapped helically, wrapped in twisted pairs, or arranged in another configuration. Here, six conductors 62 are shown, but more or fewer conductors 62 can be used. The covering can be disposed about the conductors 62 to reduce friction, thereby increasing the longevity of the driveline 22. The covering can be formed, for example, of polytetrafluoroethylene (PTFE) or fluorinated ethylene propylene (FEP) and can be applied as a tape wrapped about the conductors 62. The inner jacket 280 can be extruded onto the covering as a layer of, for example, silicone or silicone copolymer. Alternatively, polycarbonate-urethane, silicone polycarbonate-urethane, or other thermoplastics and copolymers can be used.

Located over the inner jacket 280, the armor layer 282 provides resistance to cuts, flexure failure, and other damage. The armor layer 282 can be a braided material or mesh composed of, for example, aramid fibers or para-aramid fibers. The outer jacket 284 is extruded over the armor layer 282 to form the exterior of the driveline 22. The outer jacket 284 can be formed of a silicone elastomer or other biocompatible polymer.

To facilitate a secure connection with the electrically conductive pins 320 of the blood pump 20, the end 63 of each conductor 62 is inserted into one of the ferrules 64. The ferrules 64 are crimped onto the electrical conductors 62 to establish mechanical and electrically conductive connections. The ferrules 64 can be formed of a corrosion-resistant metal, for example, platinum or a platinum-iridium alloy. The ferrules 64 and the pins 320 can be formed of the same electrically-conductive material, which reduces the potential for corrosion or differing rates of thermal expansion.

Figure 8B:
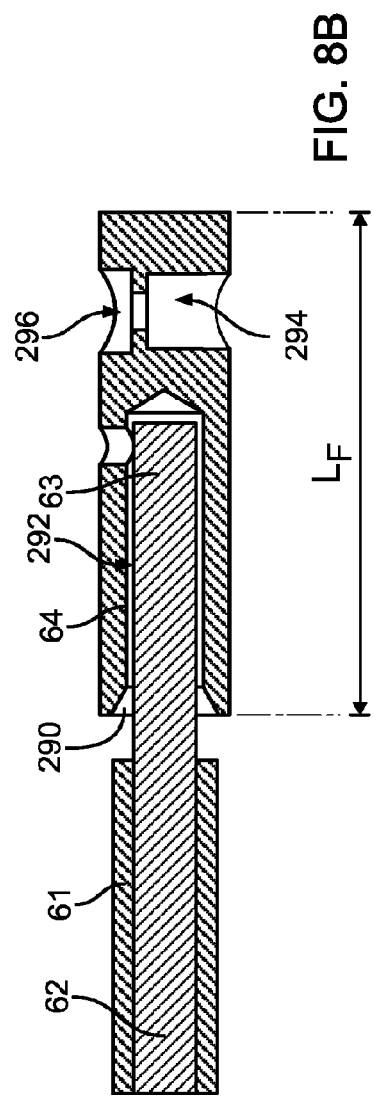
FIG. 8B is a cross-sectional view of a conductor of the driveline attached to one of the ferrules.

Referring to FIG. 8B, each ferrule 64 includes a chamfered end 290, which facilitates insertion of stranded wire. Along a length, $L_F$, of each ferrule 64, the ferrule 64 defines a space 292 that receives an end 63 of the conductor 62. Perpendicular to the length, $L_F$, the ferrule 64 also defines a space 294 that receives one of the pins 320 and a space 296 that facilitates welding of the ferrule 64 to the pin 320.

Figure 9:
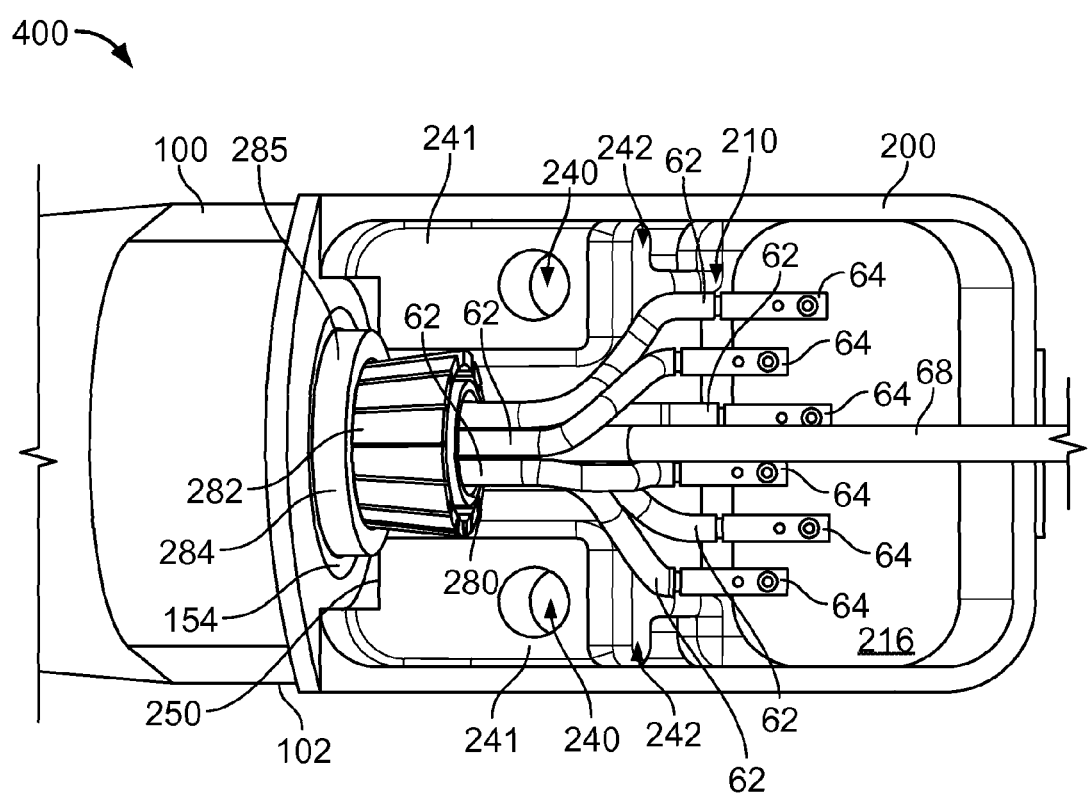
FIG. 9 is top view of conductors of the driveline arranged within the rigid member.

Referring to FIG. 9, in the completed cable assembly 400, each component of the driveline 22 extends through the internal passage 110 into the compartment 210 of the rigid member 200. The outer jacket 284 has a circumferential end 285 that engages with the surfaces 250 setting the position of the driveline 22 relative to the strain relief assembly 24. The armor layer 282, the inner jacket 280, and the conductor covering terminate in the compartment 210, for example, between the raised portions 241 of the rigid member 200. The conductors 62 are spaced apart and arranged with the ferrules 64 located over the opening 216. The inner strength member 68 initially extends outside the compartment 210, but is later terminated within the compartment 210 after the cable assembly 400 is attached to the pump housing 30.

Figure 10A:
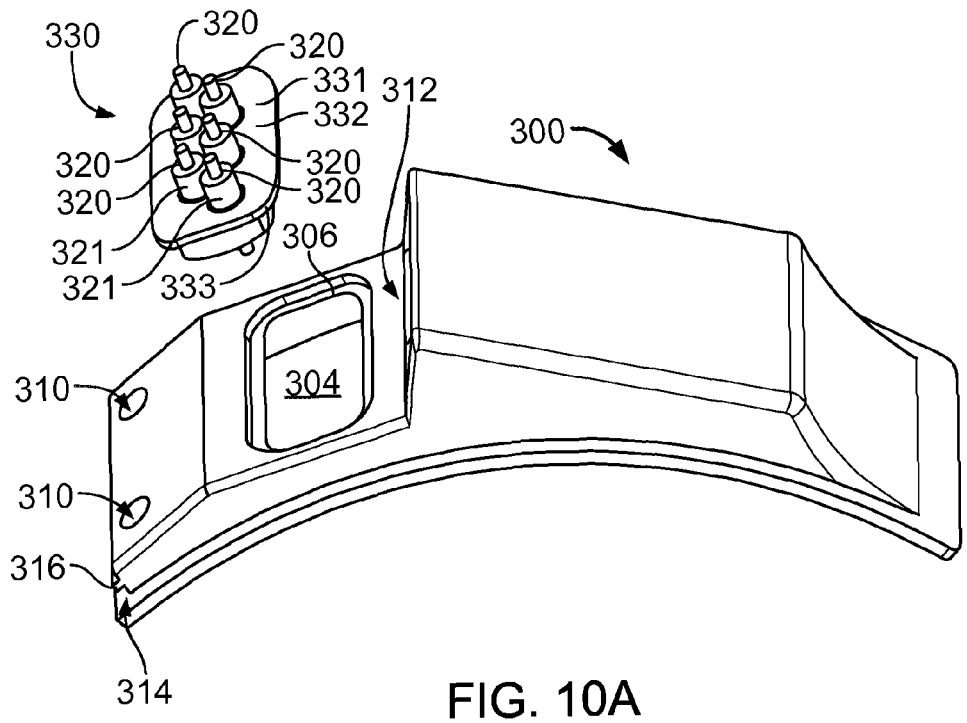
FIG. 10A is an exploded perspective view of a boss of the pump housing and a feed-through component.

Referring to FIG. 10A, the boss 300 provides attachment features for mechanically connecting to the cable assembly 400, for example, slots or grooves 312, 314 that respectively receive the tabs 230, 232 of the rigid member 200. The boss 300 also defines threaded holes 310 that receive the screws 80. The threaded holes 310 are defined only partially through the boss 300 to preserve the hermetic seal of the pump housing 30.

In some implementations, the boss 300 is separate from the upper portion 32 of the pump housing 30 (FIG. 2). After the boss 300 is formed, the boss 300 can be welded to the outer wall 38 of the pump housing 30 to form a hermetic seal. The mechanical connection of the cable assembly 400 to the boss 300 secures the cable assembly 400 to the pump housing 30.

The boss 300 defines an opening 304 that receives a hermetic feed-through component 330 that, for example, transmits electrical signals into a hermetically sealed compartment. The boss 300 includes a recessed shelf 306 around the opening 304 that engages a flange 333 of the feed-through component 330. When the flange 333 is seated against the shelf 306, the feed-through component 330 is welded to the boss 300 to form a hermetic seal around the feed-through component 330 (FIG. 10B).

Forming the feed-through component 330 and the boss 300 as separate components can facilitate manufacturing, as different process steps and temperatures may be needed to form the different components. For example, high temperature processes can be used to form the feed-through component 330 without warping or stressing the boss 300. In addition, the separate components can facilitate assembly of the pump housing 30. For example, the boss 300 is first welded to the upper portion 32 of the pump housing 30. Electrical connections are then established between the inner pump electronics and the pins 320 before the feed-through component 330 is welded to the boss 300.

The feed-through component 330 includes the pins 320, disposed on a body component 331 that is formed of the same material as the boss 300, for example, titanium. Electrical signals applied to the pins 320 are transmitted through the feed-through component 330 to the motor and other electronics sealed within the pump housing 30. Thus, the pins 320 are configured to transmit electrical signals between the hermetically sealed compartment that houses the motor and a location outside the hermetically sealed compartment, for example, to the compartment 210. The pins 320 extend perpendicular to an outer surface 332 of the feed-through component 330, in a direction that is substantially radially outward from outer wall 38 of the pump housing 30 (e.g., within 20 degrees of, or within 10 degrees of a radial direction).

Figure 10B:
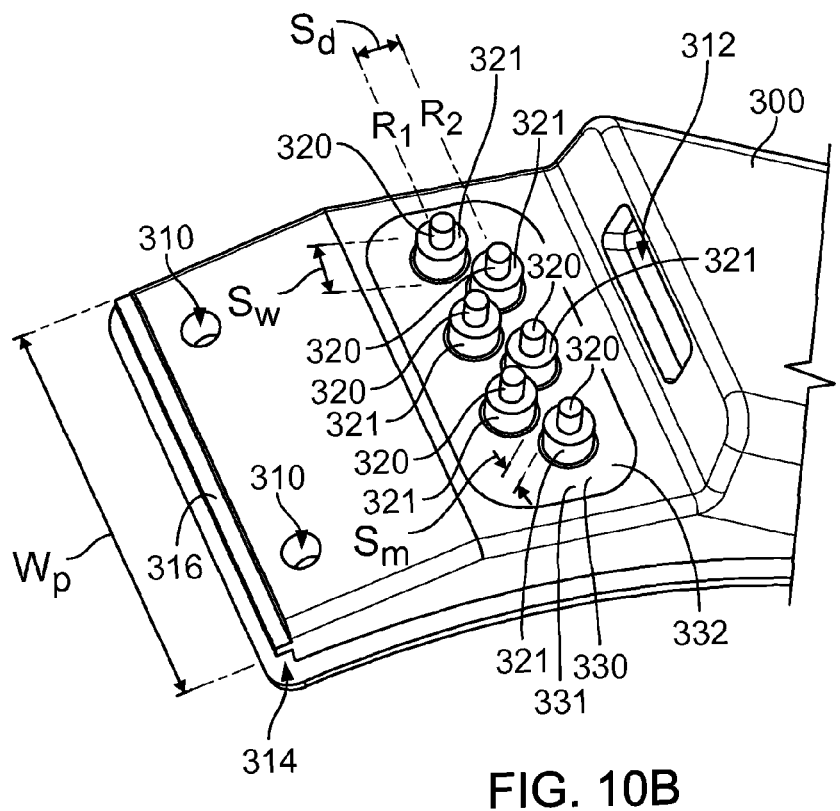
FIG. 10B is a perspective view of the boss and the feed-through component.

Referring to FIG. 10B, each pin 320 is surrounded by a sheath 321 that limits the potential for electrical shorts to the body component 331. Each sheath 321 also acts as a leak barrier, impeding moisture from entering the space between the corresponding pin 320 and the body component 330. The sheaths 321 can be formed of ceramic, for example, an alumina ceramic, a polycrystalline ceramic, or both. The sheaths 321 can each be surrounded by a sealing layer of ceramic or ceramic component that forms a hermetic seal and acts as a dielectric, as described further below. In some implementations, rather than forming sheaths about individual pins 320, a portion of the body component 331 (e.g., a central portion on which multiple pins 320 are disposed) can be formed of ceramic, glass, or another dielectric material.

A minimum spacing, $S_m$, can be maintained between the sheaths 321 to maintain desired dielectric characteristics. To minimize a width, $W_p$, across which the pins 320 are positioned (while maintaining the minimum spacing, $S_m$), the pins 320 can be arranged offset from each other. For example, the pins 320 can be disposed in two rows, $R_1$, $R_2$, that are offset from each other, for example, spaced apart by a distance, $S_W$, in width and spaced apart by a distance, $S_d$, in depth. By staggering or alternating the positions of the pins 320 in this manner, a smaller overall width, $W_p$, is achieved than would be possible by aligning the pins 320 in a single row. In some implementations, more than two rows of staggered pins can be configured for purpose of minimizing width, $W_p$. In some implementations, a single row of pins may be provided when it is not desired to minimize the width, $W_p$, and pins can alternatively be provided in an arrangements other than in rows.

Figure 11A:
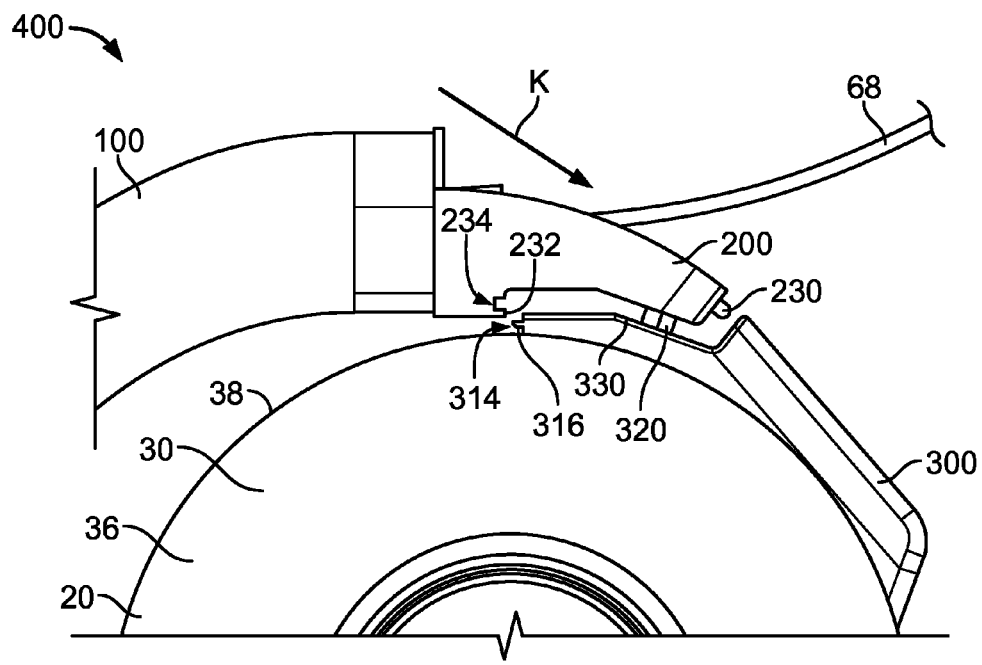
FIGS. 11A and 11B are views illustrating engagement of the rigid member with the boss.

Referring to FIG. 11A, the cable assembly 400 attaches to the pump housing 30 by engaging the boss 300. First, the rigid member 200 is positioned with the opening 216 located over the pins 320. Movement in the direction of arrow K causes the tab 230 to enter the groove 312 in the boss 300. Continuing the motion of the rigid member 200 relative to the boss 300 inserts the tab 232 in the groove 314, and simultaneously inserts the tab 316 of the boss 300 in the groove 234 of the rigid member 200, reaching the orientation shown in FIG. 11B.

Figure 11B:
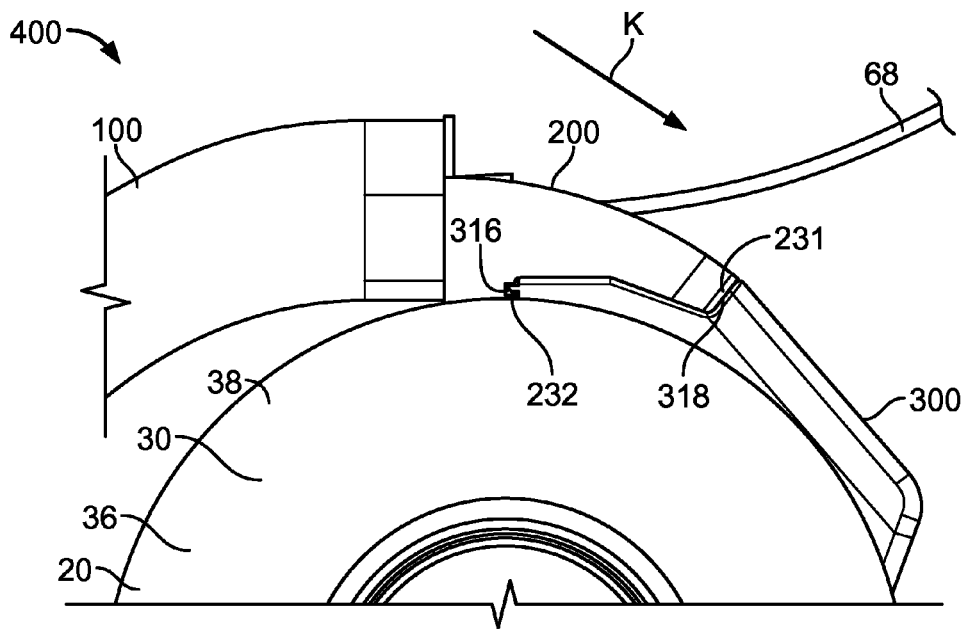

Referring to FIG. 11B, the cable assembly 400 is shown fully seated against the boss 300. The engagement of the tabs 230, 232, 316 and the corresponding grooves 312, 314, 234 limits removal of the cable assembly 400 by forces away from the pump housing 30. The proximal end 231 of the rigid member 200 engages a corresponding surface 318 of the boss 300 to limit further travel of the rigid member 200 relative to the boss 300 in the direction of arrow K.

Figure 12:
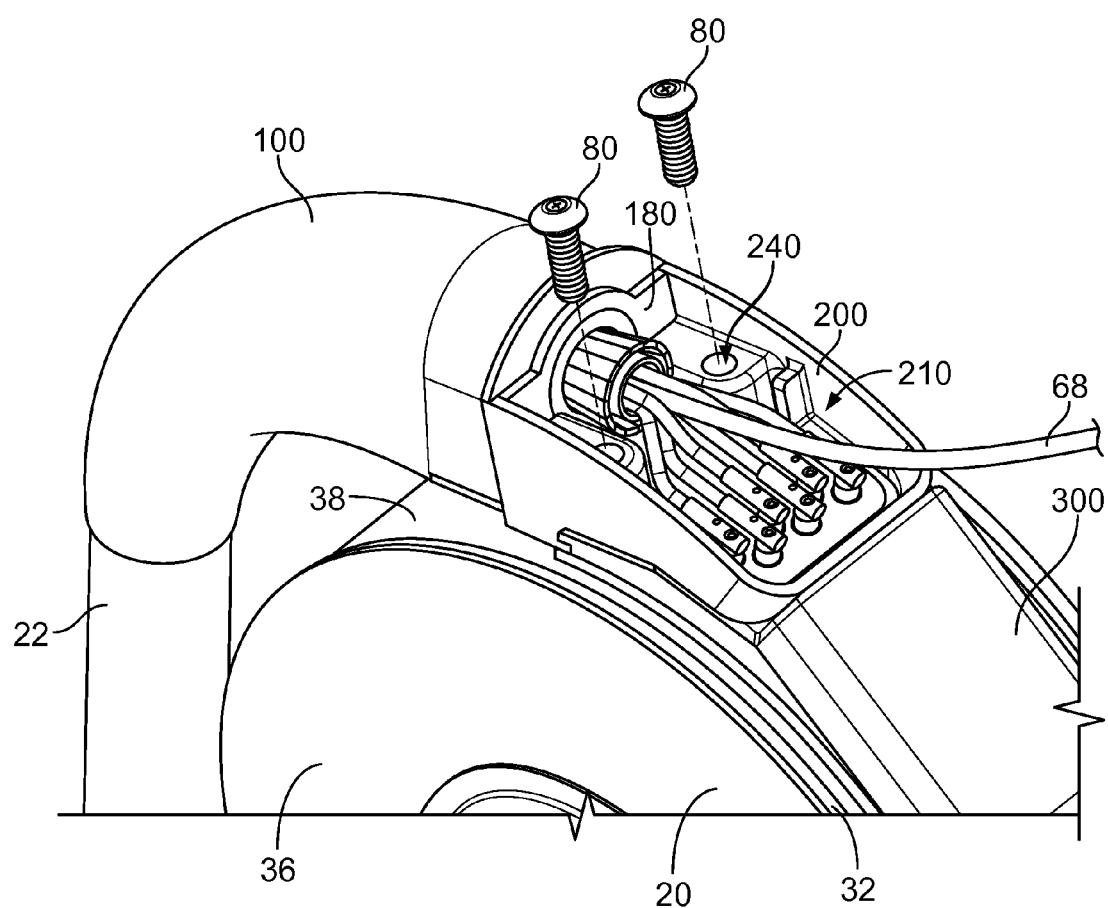
FIG. 12 is a perspective view illustrating engagement of screws with the rigid member and the pump housing.

Referring to FIG. 12, with the cable assembly 400 seated against the boss 300, the screws 80 are inserted to secure the position of the rigid member 200 relative to the boss 300. The screws 80 are inserted through the holes 240 defined in the rigid member 200 and into the threaded holes 310 defined in the boss 300. In some implementations, shear pins can be used in place of screws.

Figure 13A:
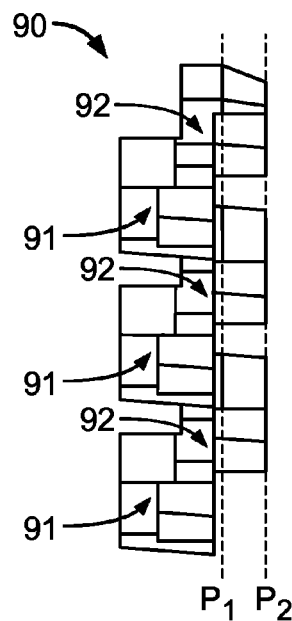
FIG. 13A is a top view of a ferrule carrier.

Referring to FIG. 13A, after the screws 80 are inserted, the ferrule carrier 90 is placed over the ferrules 64, orienting the ferrules 64 relative to each other and relative to the pins 320 that now extend into the compartment 210. The ferrule carrier 90 is formed of an electrically non-conductive material, such as plastic.

The ferrule carrier 90 defines parallel channels 91, 92 that receive ends of the ferrules 64. The channels 91, 92 arrange ends of the ferrules 64 at alternating positions $P_1$, $P_2$, aligned with the positions of the corresponding pins 320. The ferrule carrier 90 also spaces apart the ferrules 64 to avoid unwanted electrical connections between the ferrules 64, and secures the pins of the wires against the ferrules onto the cable boss.

Figure 13B:
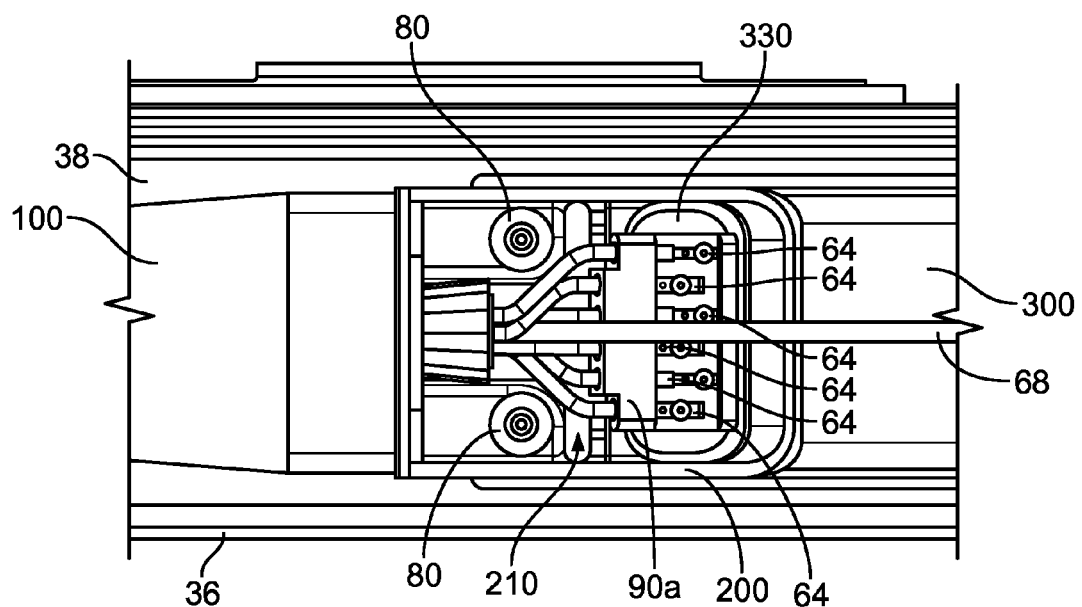
FIG. 13B is a top view of the ferrule carrier engaged within the rigid member.

Referring to FIG. 13B, the ferrules 64 are shown being aligned by an alternative ferrule carrier 90a. The alternative ferrule carrier 90a extends along the entire length of the ferrules 64, and positions the ferrules 64 relative to each other as described above for the ferrule carrier 90.

The ferrules 64 are each engaged to the corresponding pins 320 to establish electrical connections between the conductors 62 and the blood pump 20. Each ferrule 64 receives one of the pins 320 in the space 294 (FIG. 8B). The ferrules 64 are then welded to the pins 320 while the ferrule carrier 90 maintains the proper alignment. The ferrules 64 and pins 320 can be laser welded to form an electrical connection and a mechanical connection. After the ferrules 64 and the pins 320 are welded together, the ferrule carrier 90a (or the ferrule carrier 90) can be removed from the compartment 210. The welds maintain the position of the ferrules 64 relative to the pins 320.

In some implementations, the ferrule carrier 90 remains positioned on the ferrules 64 after the ferrules 64 and pins 320 are welded, as other terminations are made in the compartment 210. When the terminations are complete, the potting plug 500 can be formed about the ferrule carrier 90 such that it is secured within the compartment 210.

Figure 14A:
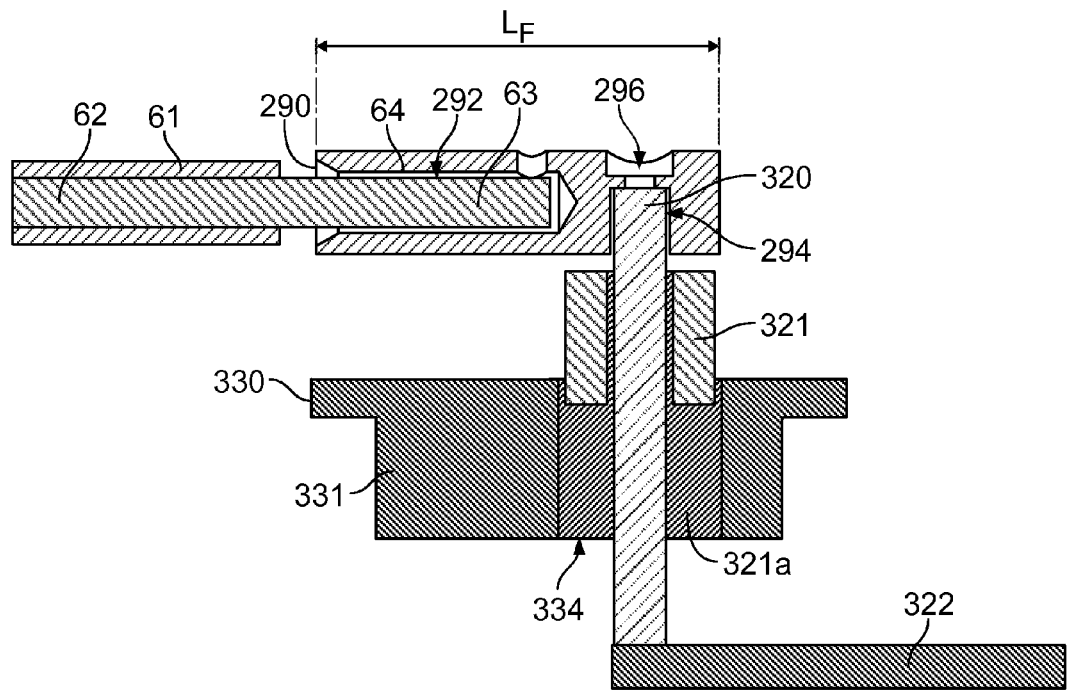
FIG. 14A is a cross-sectional view of one of the conductors of the driveline, one of the ferrules, and the feed-through component.
Figure 14B:
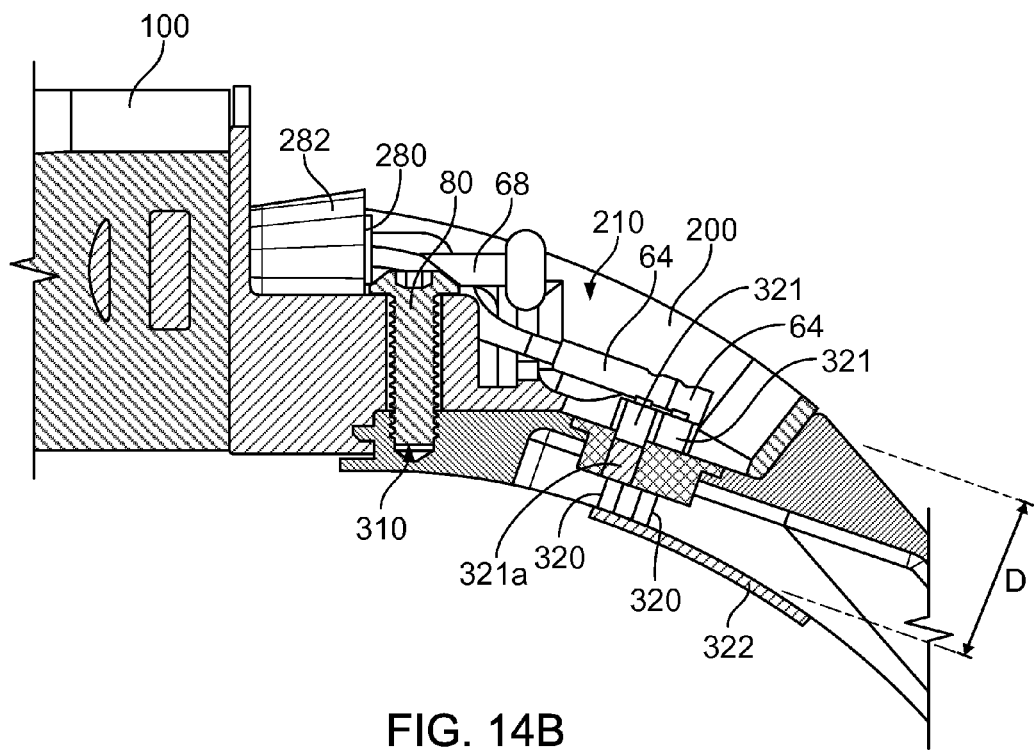
FIG. 14B is a side cutaway view of the strain relief assembly and the driveline connected to the pump housing.

Referring to FIGS. 14A and 14B, the connections between the ferrules 64 and the pins 320 are made in the compartment 210 of the rigid member 200, with the conductors 62 and the ferrules 64 oriented perpendicular to the pins 320. By connecting the pins 320 and ferrules 64 perpendicular to each other, the connections can be made within a small radial distance, D, outward from the pump housing 30. In some implementations, the connections can be made with a radial distance, D, from the pump housing 30 of approximately 0.225 inches or less.

On the interior of the pump housing 30, the pins 320 can be connected to a flexible printed circuit 322 that extends substantially perpendicular to the pins 320. In some implementations, the angle of the printed circuit 322 with the pins 320 is between 70 degrees and 110 degrees, or between 80 degrees and 100 degrees. For example, the printed circuit 322 can extend along an inner circumference of the pump housing 30 and terminate in a rigid printed circuit board-type termination. In this manner, two 90-degree turns can be made in the conductive path, in the distance, D, that generally corresponds to a length of the pins 320.

As shown in FIG. 14A, the feed-through component 330 includes ceramic components 321a which each provides a hermetic seal between one of the pins 320, the corresponding sheath 321, and the body component 331. The ceramic component 321a is located at least partially within the body component 331 and extends about one of the pins 320. The ceramic component 321a also fills gaps between the sheath 321 and the pin 320, and between the sheath 321 and the body component 331. Each ceramic component 321a also acts as a dielectric, limiting the potential for electrical shorts between the body component 331 and the pin 320 extending through the ceramic component 321a. The ceramic component 321a also impedes dendritic formations about the pins 320 that otherwise may occur due to moisture. In some implementations, the ceramic component 321a is formed of a polycrystalline ceramic material.

The ceramic component 321a is formed in a space 334 defined in the body component 331. Each sheath 321 is formed, for example, by machining or milling an alumina ceramic material. To form the ceramic component 321a, the sheath 321 and the pin 320 are positioned such that the pin 320 extends through the space 334 and the sheath 321 extends at least partially into the space 334. A ceramic powder, for example, a polycrystalline ceramic powder, is packed into the space 334 about the pin 320. The ceramic powder is heated until liquefied, permitting liquefied material to fill gaps between the sheath 321 and the pin 320, and between the sheath 321 and the body component 331. The ceramic material is then cooled, and it solidifies to form the ceramic 321a that hermetically seals the space 334. In some implementations, the ceramic material of the ceramic component 321a forms a chemical bond with materials of the body component 331, the sheath 321, and/or the pin 320. For example, a chemical bond can be formed with a titanium oxide layer of the body component 331 and with a platinum or platinum alloy material of the pin 320.

As an alternative to using the sheath 321 and forming the ceramic component 321a in the body component 331, a preformed ceramic component may be used, for example, a single ceramic component that extends through the body component 331. After the ceramic component is positioned about a pin 320 and within the space 334 in the body component 331, brazing can be used to hermetically seal the interface between the body component 331 and the ceramic component, and also hermetically seal the interface between the ceramic component and the pin 320. During brazing, gold, a gold alloy, or another filler material may be used to form wetted connections between the components.

Figure 15A:
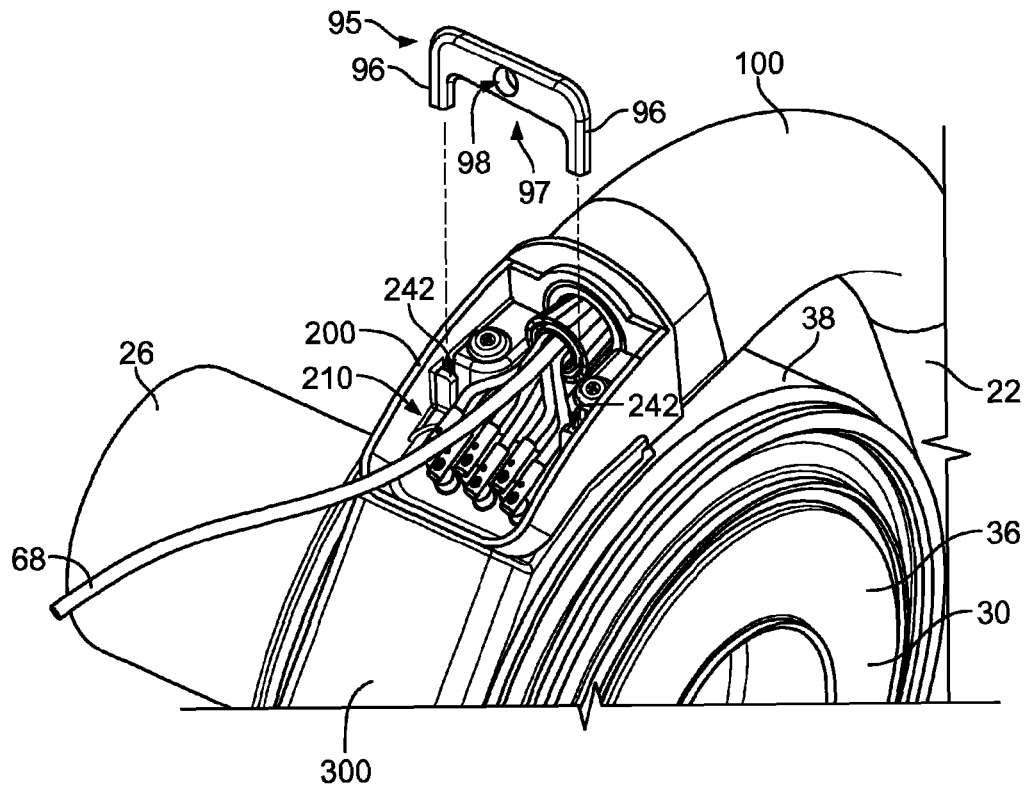
FIGS. 15A, 15B, and 15C perspective views illustrating installation of an anchor.

Referring to FIG. 15A, after the electrical connections are established, the anchor 95 is placed in the compartment 210. During insertion, the anchor 95 travels radially inward toward the pump housing 30, such that two arms 96 of the anchor 95 are received in corresponding slots 242 of the rigid member 200. The anchor 95 defines a space 97 between the arms 96 such that insertion of the anchor 95 does not interfere with the conductors 62 in the compartment 210. In some implementations, the anchor 95 is formed of titanium.

Figure 15B:
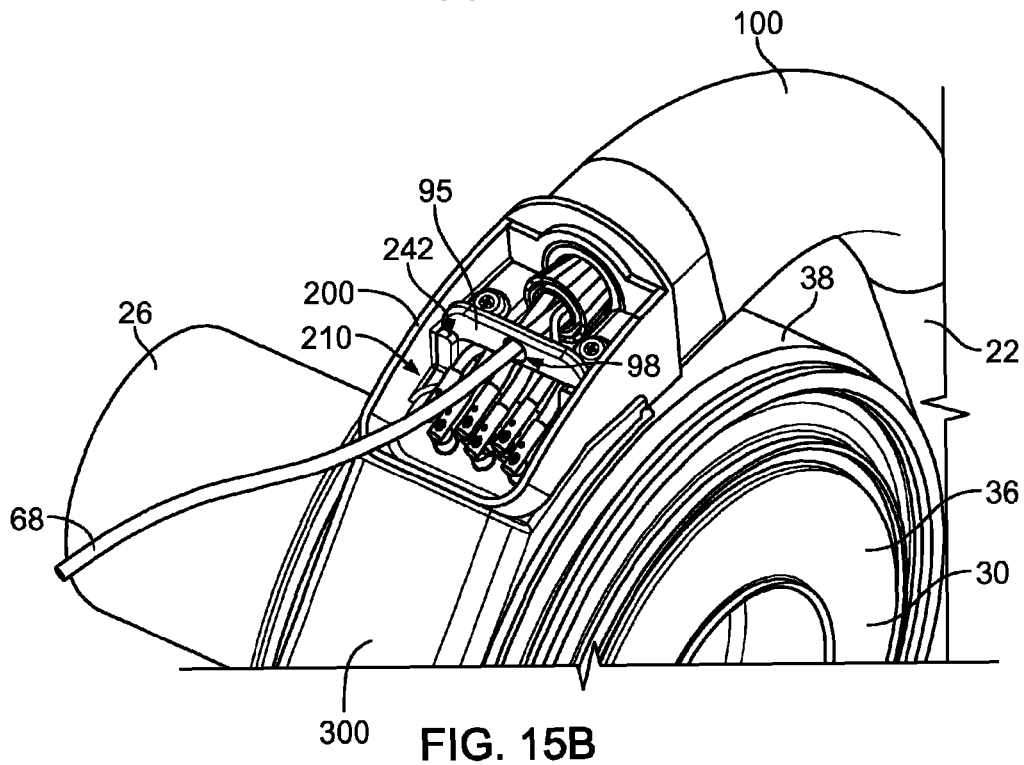

Referring to FIG. 15B, the anchor 95, when disposed in the slots 242, extends radially outward from outer wall 38 the pump housing 30 and substantially perpendicular to the internal passage 110 of the flexible member 100. For example, in some implementations, the angle between the anchor 95 and the pump housing 30 can be between 70 degrees and 110 degrees, or between 80 degrees and 100 degrees. The anchor 95 defines an opening 98 through which the inner strength member 68 is threaded.

Figure 15C:
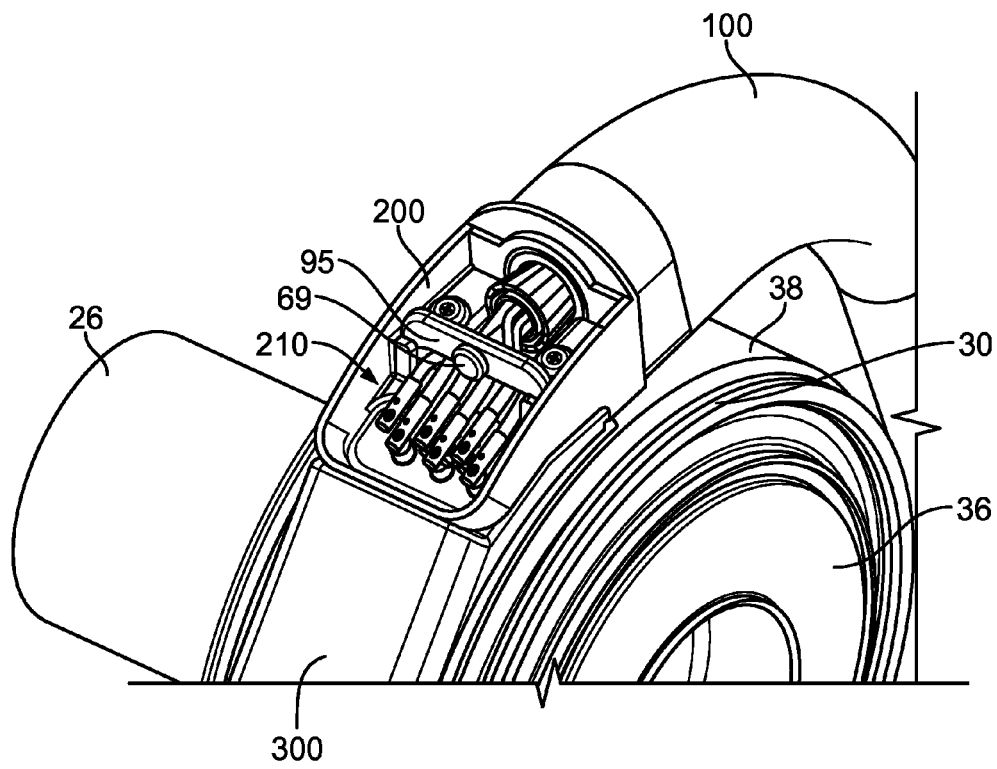

Referring to FIG. 15C, the inner strength member 68 is axially loaded to reduce slack, and then the inner strength member 68 is terminated in the compartment 210. For example, the inner strength member 68 can be terminated with a knot such that an end 69 of the inner strength member 68 is larger than the opening 98 in the anchor 95. Axial loads on the driveline 22 are transmitted through the inner strength member 68 to the anchor 95, thus avoiding or reducing axial loads on the conductors 62 or the potting plug 500, which is subsequently formed in the compartment 210. As such, the anchor 95 provides a compression force to secure the wires against the cable boss in the compartment 210 and also absorbs tension forces or axial loads exerted on the driveline 22 that are transmitted through the inner strength member 68.

Figure 15D:
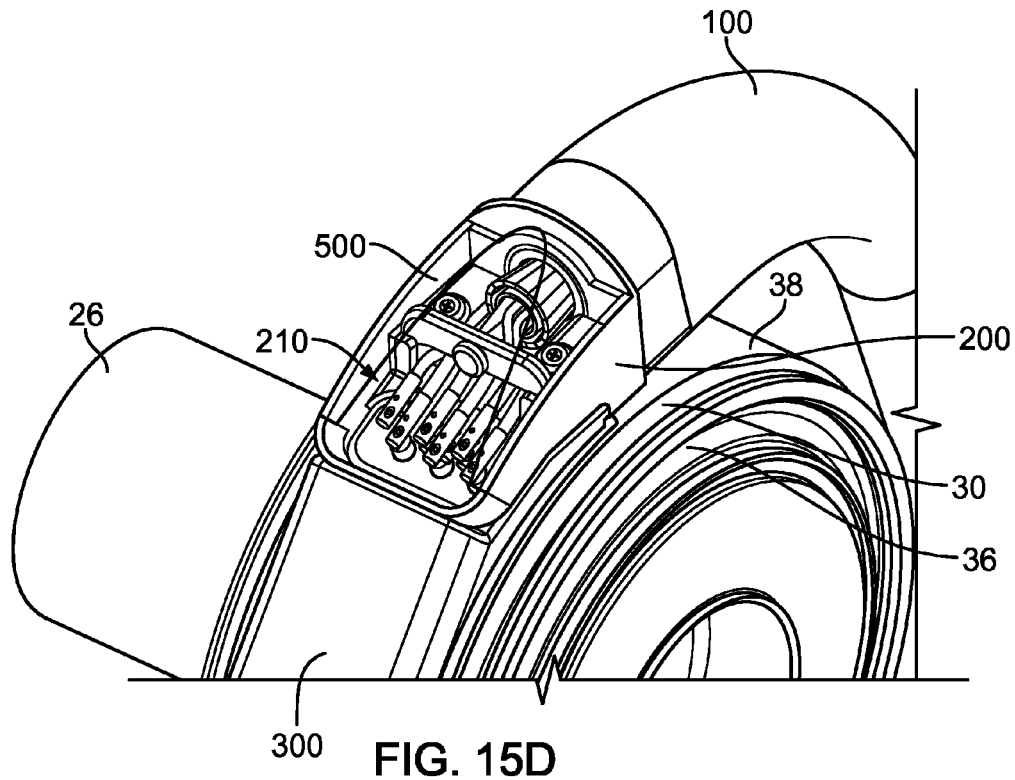
FIG. 15D is a perspective view illustrating potting within the rigid member.

Referring to FIG. 15D, potting is introduced into the compartment 210 to capture the terminations of the driveline 22. In some implementations, the potting is a UV-cured epoxy that is applied as a liquid. The potting fills the compartment 210, surrounding the conductors 62, ferrules 64, and pins 320. The potting can be exposed to UV light or a heat cycle to cure the potting and form the potting plug 500. As further examples, the potting can be a silicone encapsulant, a thermoset plastic material, or a two-part epoxy.

The potting plug 500 captures the ends of the armor layer 282, the inner jacket 280, the conductors 62 and all other components within the compartment 210. The potting plug 500 maintains the positions of the conductors 62, the ferrules 64, and the pins 320 to protect the electrical connections of the driveline 22 with the blood pump 20. The potting plug 500 also supports the mechanical connections of the cable assembly 400 to the pump housing 30, for example, by limiting removal of the screws 80 and limiting removal of the anchor 95. The potting plug 500 also acts as a moisture barrier about the ferrules 64, pins 320, and electrical connections of the driveline 22, limiting exposure to external elements such as blood, tissue, liquid, or air.

The potting plug 500 can be formed of a material that is transparent when cured. Because the compartment 210 is open in a direction facing away from the pump housing 30, the connections within the potting plug 500 can easily be visually inspected. The rigid member 200 acts as a casing or housing for the potting plug 500 formed, for example, of titanium. In some implementations, at least one side of the potting plug 500 is exposed to external elements, such as tissue and fluids. For example, the side of the potting plug 500 facing away from the blood pump 20 (for example, at the opening of the compartment 210 that faces away from the blood pump 20) is not covered by the rigid member 200 or other components of the blood pump assembly 15.

A number of implementations have been described. Nevertheless, it will be understood that various modifications may be made without departing from the spirit and scope of the claimed invention. For example, rather than using a non-axisymmetric flexible member, an axisymmetric flexible member (for example, one having a generally circular cross-sectional geometry along its length) can be used in a strain relief assembly.

In addition, the mechanisms described above can be used to electrically and mechanically connect a driveline cable assembly to a pump that has a different shape than the pump 20. The same mechanisms and strain relief techniques can be used for connections of cables to any implanted component, or to a battery, controller, or other component of a ventricular assist system. A driveline cable assembly can be attached at any outer surface of a pump housing. The strain relief assembly can be shaped to extend along one or more sides of the pump housing, and can generally track the outer contours of the pump housing. Thus the strain relief assembly can have a shape, size, and/or radius of curvature that matches the outer dimensions of a corresponding pump.

Accordingly, other embodiments are within the scope of the following claims.

The invention claimed is:

1. A blood pump assembly comprising:
a blood pump configured for implantation; and
a cable assembly secured to the blood pump for providing power and control signals to the blood pump, the cable assembly including a strain relief assembly and a driveline,
the strain relief assembly securing the cable assembly to the blood pump and having an outer surface that is curved along a longitudinal extent of the strain relief assembly at least along an outer peripheral side of the outer surface, the strain relief assembly defining a compartment and an internal passage that leads to the compartment, and
the driveline housing a plurality of conductors that extend from the driveline through the internal passage and into the compartment.

2. The blood pump assembly of claim 1, wherein the strain relief assembly is sized and positioned to lie entirely within a transverse footprint of the blood pump.

3. The blood pump assembly of claim 1, wherein the outer surface of the strain relief assembly has an inner peripheral side opposite the outer peripheral side, the inner peripheral side facing the blood pump and being spaced apart from the blood pump.

4. The blood pump assembly of claim 3, wherein the blood pump has an outer surface facing the inner peripheral side, and the inner peripheral side has a radius of curvature along the longitudinal extent that is larger than a radius of curvature of the outer surface of the blood pump along the longitudinal extent.

5. The blood pump assembly of claim 1, wherein the pump housing includes electrical connectors that extend into the compartment.

6. The blood pump assembly of claim 5, wherein the conductors are electrically connected to the electrical connectors of the pump housing, the conductors being oriented substantially transverse to the electrical connectors.

7. The blood pump assembly of claim 1, wherein the conductors are secured within the compartment by potting.

8. The blood pump assembly of claim 1, wherein the cable assembly comprises an inner strength member that extends through the internal passage and is anchored to the strain relief assembly within the compartment.

9. The blood pump assembly of claim 1, wherein the blood pump has an outlet portion that defines an outlet axis and the cable assembly orients the driveline in a direction substantially parallel to the outlet axis, wherein the driveline is radially offset from the outlet portion by a distance of less than approximately 1 inch.

10. An implantable strain relief assembly comprising:

a first member having an annular portion and an opening defined through the annular portion, the first member having a conductor mounting portion that defines a compartment in communication with the opening; and a second member that is more flexible than the first member, the second member having an end region coupled to the annular portion and having an outer surface that is curved along a longitudinal extent of the second member at least along a side of the outer surface, the second member defining an internal passage along the longitudinal extent leading to the opening defined through the annular portion of the first member, the internal passage having a substantially constant diameter along the longitudinal extent, the second member having a wall thickness that decreases along the longitudinal extent.

11. The implantable strain relief assembly of claim 10, wherein the annular portion has an inner surface and an outer surface, and the second member is molded about the outer surface.

12. The implantable strain relief assembly of claim 10, wherein holes are defined through the annular portion and the second member extends through the holes.

13. The implantable strain relief assembly of claim 10, wherein the first member is configured to receive an anchor component in the compartment, the anchor compartment being configured to secure an end of a cable to the first member.

14. The implantable strain relief assembly of claim 10, wherein the first member includes a surface oriented perpendicular to the internal passage configured to engage a cable to limit travel of the cable through the passage.

15. An implantable strain relief device comprising:

a member having an outer surface that is curved along a longitudinal extent of the member at least along a side of the outer surface, the member defining an internal passage along the longitudinal extent having a substantially constant diameter along the longitudinal extent, the member having a wall thickness that decreases along the longitudinal extent, at least a portion of the outer surface having a cross-sectional geometry that includes a rounded portion opposite a substantially flat portion.

16. The implantable strain relief device of claim 15, wherein the outer surface is curved in an unloaded state of the member.

17. The implantable strain relief device of claim 15, wherein the member has a distal end portion that has a cross-sectional geometry that is substantially circular.

18. The implantable strain relief device of claim 15, wherein the outer surface of the member has a side that has a radius of curvature of between approximately 1 and approximately 3 inches along the longitudinal extent.

19. The implantable strain relief device of claim 15, wherein a length of the member along the longitudinal extent is between approximately 2 and approximately 4 inches.

* * * * *